(12) United States Patent
Ferree

(10) Patent No.: US 10,245,018 B2
(45) Date of Patent: *Apr. 2, 2019

(54) METHOD AND APPARATUS FOR CLOSING FISSURES IN THE ANNULUS FIBROSUS

(71) Applicant: Suture Concepts Inc., Basking Ridge, NJ (US)

(72) Inventor: Bret A. Ferree, Cincinnati, OH (US)

(73) Assignee: Suture Concepts Inc., Basking Ridge, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,391

(22) Filed: Jan. 12, 2016

(65) Prior Publication Data

US 2016/0361053 A1 Dec. 15, 2016

Related U.S. Application Data

(63) Continuation of application No. 13/464,533, filed on May 4, 2012, now Pat. No. 9,232,938, which is a
(Continued)

(51) Int. Cl.
*A61F 2/44* (2006.01)
*A61B 17/04* (2006.01)
(Continued)

(52) U.S. Cl.
CPC .... *A61B 17/0401* (2013.01); *A61B 17/06061* (2013.01); *A61B 17/06066* (2013.01);
(Continued)

(58) Field of Classification Search
CPC ............. A61F 2/442; A61F 2002/4435; A61B 17/0401
See application file for complete search history.

(56) References Cited

U.S. PATENT DOCUMENTS 3,867,728 A 2/1975 Stubstad et al.
3,875,595 A 4/1975 Froning
(Continued)

FOREIGN PATENT DOCUMENTS

EP 0700671 3/1996
EP 0722700 7/1996
(Continued)

OTHER PUBLICATIONS

Wilke, H. et al., New In Vivo Measurements of Pressures in the Intervertebral Disc in Daily Life, Spine, 24(8): 755-762, Nov. 8, 1999.
(Continued)

*Primary Examiner* — Julianna N Harvey
(74) *Attorney, Agent, or Firm* — Pandiscio & Pandiscio

(57) ABSTRACT

A method for closing a fissure in a region of tissue having an inner surface and an outer surface, the method comprising:
providing at least a pair of transverse anchor components, each transverse anchor component being coupled to at least one flexible longitudinal fixation component having a longitudinal axis;
placing the transverse anchor components relative to the inner surface of the tissue on both sides of the fissure such that an exposed end of a flexible longitudinal fixation component extends through the tissue and past the outer surface of the tissue on both sides of the fissure;
applying axial tension to the exposed ends; and
anchoring the exposed ends.

2 Claims, 16 Drawing Sheets

Related U.S. Application Data continuation of application No. 12/263,753, filed on Nov. 3, 2008, now abandoned, which is a continuation of application No. 11/811,751, filed on Jun. 12, 2007, now Pat. No. 8,075,619, said application No. 13/464,533 is a continuation-in-part of application No. 13/297,789, filed on Nov. 16, 2011, now abandoned.

(60) Provisional application No. 60/813,232, filed on Jun. 13, 2006, provisional application No. 60/847,649, filed on Sep. 26, 2006, provisional application No. 60/984,657, filed on Nov. 1, 2007, provisional application No. 61/414,186, filed on Nov. 16, 2010, provisional application No. 61/483,204, filed on May 6, 2011.

(51) Int. Cl.
*A61B 17/06* (2006.01)
*A61B 17/064* (2006.01)
*A61B 17/84* (2006.01)
*A61B 17/00* (2006.01)
*A61F 2/30* (2006.01)
*A61B 17/08* (2006.01)

(52) U.S. Cl.
CPC .. *A61B 17/06109* (2013.01); *A61B 17/06166* (2013.01); *A61F 2/442* (2013.01); *A61B 17/0485* (2013.01); *A61B 17/0487* (2013.01); *A61B 17/0644* (2013.01); *A61B 17/842* (2013.01); *A61B 2017/00849* (2013.01); *A61B 2017/00867* (2013.01); *A61B 2017/0403* (2013.01); *A61B 2017/044* (2013.01); *A61B 2017/0404* (2013.01); *A61B 2017/0409* (2013.01); *A61B 2017/0414* (2013.01); *A61B 2017/0427* (2013.01); *A61B 2017/0464* (2013.01); *A61B 2017/0496* (2013.01); *A61B 2017/061* (2013.01); *A61B 2017/0608* (2013.01); *A61B 2017/0619* (2013.01); *A61B 2017/081* (2013.01); *A61B 2017/088* (2013.01); *A61F 2002/30062* (2013.01); *A61F 2002/30075* (2013.01); *A61F 2002/3085* (2013.01); *A61F 2002/30092* (2013.01); *A61F 2002/30125* (2013.01); *A61F 2002/30166* (2013.01); *A61F 2002/30235* (2013.01); *A61F 2002/30451* (2013.01); *A61F 2002/30461* (2013.01); *A61F 2002/30677* (2013.01); *A61F 2002/30772* (2013.01); *A61F 2002/30841* (2013.01); *A61F 2002/30932* (2013.01); *A61F 2002/4435* (2013.01); *A61F 2210/0014* (2013.01); *A61F 2210/0061* (2013.01); *A61F 2220/005* (2013.01); *A61F 2220/0058* (2013.01); *A61F 2220/0075* (2013.01); *A61F 2230/0008* (2013.01); *A61F 2230/0023* (2013.01); *A61F 2230/0069* (2013.01); *A61F 2310/00365* (2013.01)

(56) References Cited

U.S. PATENT DOCUMENTS

| | | | |
|---|---|---|---|
| 4,349,921 A | 9/1982 | Kuntz | |
| 4,413,359 A | 11/1983 | Akiyama et al. | |
| 4,502,161 A | 3/1985 | Wall | |
| 4,512,338 A | 4/1985 | Balko et al. | |
| 4,532,926 A | 8/1985 | O'Holla | |
| 4,585,458 A | 4/1986 | Kurland | |
| 4,662,068 A * | 5/1987 | Polonsky | A61B 17/04 30/124 |
| 4,663,358 A | 5/1987 | Hyon et al. | |
| 4,665,906 A | 5/1987 | Jervis | |
| 4,741,330 A | 5/1988 | Hayhurst | |
| 4,744,364 A | 5/1988 | Kensey | |
| 4,772,287 A | 9/1988 | Ray et al. | |
| 4,781,190 A | 11/1988 | Lee | |
| 4,798,205 A | 1/1989 | Bonomo et al. | |
| 4,834,757 A | 5/1989 | Brantigan | |
| 4,852,568 A | 8/1989 | Kensey | |
| 4,863,477 A | 9/1989 | Monson | |
| 4,873,976 A | 10/1989 | Schreiber | |
| 4,890,612 A | 1/1990 | Kensey | |
| 4,904,260 A | 2/1990 | Ray et al. | |
| 4,911,718 A | 3/1990 | Lee et al. | |
| 4,917,704 A | 4/1990 | Frey et al. | |
| 4,932,969 A | 6/1990 | Frey et al. | |
| 4,946,378 A | 8/1990 | Hirayama et al. | |
| 4,955,908 A | 9/1990 | Frey et al. | |
| 5,002,576 A | 3/1991 | Fuhrmann et al. | |
| 5,015,255 A | 5/1991 | Kuslich | |
| 5,021,059 A | 6/1991 | Kensey et al. | |
| 5,035,716 A | 7/1991 | Downey | |
| 5,047,055 A | 9/1991 | Bao et al. | |
| 5,053,046 A | 10/1991 | Janese | |
| 5,059,206 A | 10/1991 | Winters | |
| 5,061,274 A | 10/1991 | Kensey | |
| 5,071,437 A | 12/1991 | Steffee | |
| 5,100,422 A | 3/1992 | Berguer et al. | |
| 5,108,438 A | 4/1992 | Stone | |
| 5,116,357 A | 5/1992 | Eberbach | |
| 5,122,155 A | 6/1992 | Eberbach | |
| 5,123,926 A | 6/1992 | Pisharodi | |
| 5,141,515 A | 8/1992 | Eberbach | |
| 5,147,374 A | 9/1992 | Fernandez | |
| 5,171,259 A | 12/1992 | Inoue | |
| 5,171,278 A | 12/1992 | Pisharodi | |
| 5,171,280 A | 12/1992 | Baumgartner | |
| 5,171,281 A | 12/1992 | Parsons et al. | |
| 5,176,692 A | 1/1993 | Wilk et al. | |
| 5,192,326 A | 3/1993 | Bao et al. | |
| 5,222,974 A | 6/1993 | Kensey et al. | |
| 5,254,133 A | 10/1993 | Seid | |
| 5,258,000 A | 11/1993 | Gianturco | |
| 5,258,043 A | 11/1993 | Stone | |
| 5,269,783 A | 12/1993 | Sander | |
| 5,282,827 A | 2/1994 | Kensey et al. | |
| 5,304,194 A | 4/1994 | Chee et al. | |
| 5,306,311 A | 4/1994 | Stone et al. | |
| 5,312,435 A | 5/1994 | Nash et al. | |
| 5,318,780 A | 6/1994 | Viegas et al. | |
| 5,320,633 A | 6/1994 | Allen et al. | |
| 5,320,644 A | 6/1994 | Baumgartner | |
| 5,342,393 A | 8/1994 | Stack | |
| 5,342,394 A | 8/1994 | Matsuno et al. | |
| 5,356,432 A | 10/1994 | Rutkow et al. | |
| 5,366,460 A | 11/1994 | Eberbach | |
| 5,368,602 A | 11/1994 | De La Torre | |
| 5,370,660 A | 12/1994 | Weinstein et al. | |
| 5,370,697 A | 12/1994 | Baumgartner | |
| 5,376,693 A | 12/1994 | Viegas et al. | |
| 5,383,477 A | 1/1995 | Dematteis | |
| 5,383,905 A | 1/1995 | Golds | |
| 5,390,683 A | 2/1995 | Pisharodi | |
| 5,397,331 A | 3/1995 | Himpens et al. | |
| 5,397,332 A | 3/1995 | Kammerer et al. | |
| 5,405,360 A | 4/1995 | Tovey | |
| 5,425,772 A | 6/1995 | Brantigan | |
| 5,425,773 A | 6/1995 | Boyd et al. | |
| 5,437,631 A | 8/1995 | Janzen | |
| 5,456,720 A | 10/1995 | Schultz et al. | |
| 5,464,407 A | 11/1995 | Mcguire | |
| 5,500,000 A | 3/1996 | Feagin et al. | |
| 5,507,754 A | 4/1996 | Green et al. | |
| 5,514,180 A | 5/1996 | Heggeness et al. | |
| 5,520,700 A | 5/1996 | Beyar et al. | |
| 5,531,759 A | 7/1996 | Kensey et al. | |
| 5,534,028 A | 7/1996 | Bao et al. | |

(56) References Cited

U.S. PATENT DOCUMENTS

| | | |
|---|---|---|
| 5,534,030 A | 7/1996 | Navarro et al. |
| 5,540,715 A | 7/1996 | Katsaros et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,587,175 A | 12/1996 | Viegas et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,645,084 A | 7/1997 | McKay |
| 5,645,597 A | 7/1997 | Krapiva |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,709,854 A | 1/1998 | Griffith-Cima et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,718,862 A | 2/1998 | Thompson |
| 5,725,577 A | 3/1998 | Saxon |
| 5,728,150 A | 3/1998 | McDonald et al. |
| 5,730,744 A | 3/1998 | Justin et al. |
| 5,733,337 A | 3/1998 | Carr, Jr. et al. |
| 5,743,917 A | 4/1998 | Saxon |
| 5,746,755 A | 5/1998 | Wood et al. |
| 5,746,765 A | 5/1998 | Kleshinski et al. |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,785,705 A | 7/1998 | Baker |
| 5,800,549 A | 9/1998 | Bao et al. |
| 5,800,550 A | 9/1998 | Sertich |
| 5,801,033 A | 9/1998 | Hubbell et al. |
| 5,810,851 A | 9/1998 | Yoon |
| 5,823,994 A | 10/1998 | Sharkey et al. |
| 5,824,008 A | 10/1998 | Bolduc et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,827,328 A | 10/1998 | Buttermann |
| 5,836,315 A | 11/1998 | Benderev et al. |
| 5,843,084 A | 12/1998 | Hart et al. |
| 5,846,261 A | 12/1998 | Kotula et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,879,366 A | 3/1999 | Shaw et al. |
| 5,888,220 A | 3/1999 | Felt et al. |
| 5,888,226 A | 3/1999 | Rogozinski |
| 5,893,889 A | 4/1999 | Harrington |
| 5,916,225 A | 6/1999 | Kugel |
| 5,919,235 A | 7/1999 | Husson et al. |
| 5,922,026 A | 7/1999 | Chin |
| 5,928,284 A | 7/1999 | Mehdizadeh |
| 5,935,147 A | 8/1999 | Kensey et al. |
| 5,954,716 A | 9/1999 | Sharkey et al. |
| 5,954,767 A | 9/1999 | Pajotin et al. |
| 5,957,939 A | 9/1999 | Heaven et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 6,001,130 A | 12/1999 | Bryan et al. |
| 6,007,570 A | 12/1999 | Sharkey et al. |
| 6,007,575 A | 12/1999 | Samuels |
| 6,019,793 A | 2/2000 | Perren et al. |
| 6,024,754 A | 2/2000 | Engelson |
| 6,027,527 A | 2/2000 | Asano et al. |
| 6,126,682 A | 10/2000 | Sharkey et al. |
| 6,140,452 A | 10/2000 | Felt et al. |
| 6,146,380 A | 11/2000 | Racz et al. |
| 6,180,848 B1 | 1/2001 | Flament et al. |
| 6,183,518 B1 | 2/2001 | Ross et al. |
| 6,206,921 B1 | 3/2001 | Guagliano et al. |
| 6,224,630 B1 | 5/2001 | Bao et al. |
| 6,245,107 B1 | 6/2001 | Ferree |
| 6,371,990 B1 | 4/2002 | Ferree |
| 6,402,750 B1 | 6/2002 | Atkinson et al. |
| 6,425,919 B1 * | 7/2002 | Lambrecht ............ A61B 5/1076 623/17.16 |
| 6,428,576 B1 | 8/2002 | Haldimann |
| 6,436,143 B1 | 8/2002 | Ross et al. |
| 6,482,235 B1 | 11/2002 | Lambrecht et al. |
| 6,511,491 B2 | 1/2003 | Grudem et al. |
| 6,733,531 B1 | 5/2004 | Trieu |
| 6,878,167 B2 | 4/2005 | Ferree |
| 7,004,970 B2 | 2/2006 | Cauthen, III et al. |
| 7,201,774 B2 | 4/2007 | Ferree |
| 7,338,525 B2 | 3/2008 | Ferree |
| 7,947,080 B2 | 5/2011 | Ferree |
| 2002/0123750 A1 | 9/2002 | Eisermann et al. |
| 2002/0198599 A1 | 12/2002 | Haldimann |
| 2003/0074075 A1 | 4/2003 | Thomas et al. |
| 2003/0114930 A1 | 6/2003 | Lim et al. |
| 2003/0158604 A1 * | 8/2003 | Cauthen, III ............ A61F 2/441 623/17.16 |
| 2004/0260397 A1 | 12/2004 | Lambrecht et al. |
| 2005/0125071 A1 | 6/2005 | Nahleili |
| 2005/0143826 A1 | 6/2005 | Zucherman et al. |
| 2005/0261710 A1 | 11/2005 | Sakamoto et al. |
| 2006/0217747 A1 | 9/2006 | Ferree |
| 2007/0067040 A1 | 3/2007 | Ferree |
| 2007/0135920 A1 | 6/2007 | Ferree |
| 2007/0167951 A1 | 7/2007 | Ainsworth et al. |
| 2007/0276494 A1 | 11/2007 | Ferree |
| 2007/0288040 A1 | 12/2007 | Ferree |
| 2008/0177298 A1 | 7/2008 | Zucherman et al. |
| 2008/0243249 A1 | 10/2008 | Kohm et al. |
| 2010/0016889 A1 | 1/2010 | Ferree |
| 2010/0069957 A1 | 3/2010 | Abuzaina et al. |
| 2011/0034975 A1 | 2/2011 | Ferree |

FOREIGN PATENT DOCUMENTS

| | | |
|---|---|---|
| EP | 0277678 | 8/1998 |
| EP | 1719463 | 11/2006 |
| EP | 1787604 | 5/2007 |
| FR | 2639823 | 6/1990 |
| WO | WO 95/31946 | 11/1995 |
| WO | WO 95/34331 | 12/1995 |
| WO | WO 97/26847 | 7/1997 |

(56) References Cited

FOREIGN PATENT DOCUMENTS

| | | |
|---|---|---|
| WO | WO 97/30638 | 8/1997 |
| WO | WO 98/17190 | 4/1998 |
| WO | WO 98/20939 | 5/1998 |
| WO | WO 98/34552 | 8/1998 |
| WO | WO 99/00074 | 1/1999 |
| WO | WO 99/02108 | 1/1999 |
| WO | WO 99/02214 | 1/1999 |
| WO | WO 99/03422 | 1/1999 |
| WO | WO 99/30651 | 6/1999 |
| WO | WO 99/47058 | 9/1999 |
| WO | WO 99/61084 | 12/1999 |
| WO | WO 99/61840 | 12/1999 |
| WO | WO 99/62439 | 12/1999 |
| WO | WO 00/42953 | 7/2000 |
| WO | WO 00/62832 | 10/2000 |
| WO | WO 01/10316 | 2/2001 |
| WO | WO 01/10318 | 2/2001 |
| WO | WO 01/21246 | 3/2001 |
| WO | WO 01/28464 | 4/2001 |
| WO | WO 01/45577 | 6/2001 |
| WO | WO 2010/062971 | 6/2010 |

OTHER PUBLICATIONS

Proceedings 14th Annual meeting North American Spine Society, Oct. 1999.

Proceedings 13th Annual Meeting North American Spine Society, Oct. 1998.

Goel, V.K., et al., "Mechanical Properties of Lumbar Spinal Motion Segments as Affected by Partial Disc Removal," Spine, 11(10): 1008-1012, (1986).

Ahlgren, B.D., et al., "Anular Incision Technique on the Strength and Multidirectional Flexibility of the Healing Intervertebral Disc," Spine, 19(8): 948-954, (1994).

Barr, J.S., "Ruptured Intervertebral Disc and Sciatic Pain," J. of Bone and Joint Surgery, 29, (2): 429-437 (1947).

Postacchini, F., "Spine Update Results of Surgery Compared With Conservative Management for Lumbar Disc Herniations," Spine, 21 (11): 1383-1387, (1996).

Rogers, L.A., "Experience with Limited versus Extensive Disc Removal in Patients Undergoing Microsurgical Operations for Rupertured Lumbar Discs," Neurosurgery, 22 (1): 82-85, (1988).

Brinckmann, P., et al., "Change of Disc Height, Radial Disc Bulge, and Intradiscal Pressure From Discectomy an in Vitro Investigation on Human Lumbar Discs," Spine, 16(6): 641-646, (1991).

Balderston, R.A., et al., "The Treatment of Lumbar Disc Herniation: Simple Fragment Excision Versus Disc Space Curettage," J. of Spinal Disorders, 4(1): 22-25 (1991).

Hanley, E.N., Jr., et al., "The Development of Low-Back Pain after Excision of a Lumbar Disc," J. of Bone and Joint Surgery, 71A(5): 719-721, (1989).

Tulberg, T., et al., "Incision of the Annulus Fibrosus Induces Nerve Root Morphologic, Vascular and Functional Changes," Spine, 18(7): 843-850, (1993).

Heggeness, M.H., et al., "Discography of Lumbar Discs After Surgical Treatment for Disc Herniation," Spine, 22(14): 1606-1609, (1997).

Kayama, S., et al, "Incision of the Anulus Fibrosus Induces Nerve Root Morphologic Vascular and Functional Changes," Spine, 21(22): 2539-2543, (1996).

Yasargil, M.G., "Microsurgical Operation of Herniated Lumbar Disc," p. 81, 1977.

Tibrewal, S.B., et al., "Lumbar Intervertebral Disc Heights in Normal Subjects and Patients with Disc Herniation," Spine, 10 (5): 452-454, (1985).

Cauthen, Joseph, C., M.D., "Microsurgical Annular Reconstruction (Annuloplasty) Following Lumbar Microdiscectomy; Preliminary Report of a New Technique," Abstract for Poster Presentation, AANS/CNS Section on Disorders of the Spine and Peripheral Nerves Annual Meeting, 1999.

Husson, J. et al., Inter-Somatic Nucleoplasty by Posterior Path During Disectomy, Concept and Experimental Study, 1998.

* cited by examiner

METHOD AND APPARATUS FOR CLOSING FISSURES IN THE ANNULUS FIBROSUS

REFERENCE TO PENDING PRIOR PATENT APPLICATIONS

This patent application is a continuation of pending prior U.S. patent application Ser. No. 13/464,533, filed May 4, 2012 by Bret A. Ferree for METHOD AND APPARATUS FOR CLOSING FISSURES IN THE ANNULUS FIBROSUS, which in turn:

(1) is a continuation-in-part of prior U.S. patent application Ser. No. 12/263,753, filed Nov. 3, 2008 by Bret A. Ferree for METHODS AND APPARATUS FOR ANULUS REPAIR, which in turn: (i) is a continuation-in-part of prior U.S. patent application Ser. No. 11/811,751, filed Jun. 12, 2007 by Bret A. Ferree for DEVICES FOR DISC HERNIATION REPAIR AND METHODS OF USE, which patent application claims benefit of (a) prior U.S. Provisional Patent Application Ser. No. 60/813,232, filed Jun. 13, 2006 by Bret A. Ferree, and (b) prior U.S. Provisional Patent Application Ser. No. 60/847,649, filed Sep. 26, 2006 by Bret A. Ferree; and (ii) claims benefit of prior U.S. Provisional Patent Application Ser. No. 60/984,657, filed Nov. 1, 2007 by Bret A. Ferree;

(2) is a continuation-in-part of prior U.S. patent application Ser. No. 13/297,789, filed Nov. 16, 2011 by Bret A. Ferree for APPARATUS AND METHODS FOR CLOSURE OF FISSURES IN THE ANULUS FIBROSIS, which patent application claims benefit of prior U.S. Provisional Patent Application Ser. No. 61/414,186, filed Nov. 16, 2010 by Bret A. Ferree; and (3) claims benefit of prior U.S. Provisional Patent Application Ser. No. 61/483,204, filed May 6, 2011 by Bret A. Ferree for APPARATUS AND METHODS FOR CLOSURE OF FISSURES IN THE ANULUS FIBROSIS.

The above-identified patent applications are hereby incorporated herein by reference.

FIELD OF THE INVENTION

This invention relates to the treatment of intervertebral disc herniation and degenerative disc disease in general and, more particularly, to methods and apparatus for closing fissures in the annulus fibrosus.

BACKGROUND OF THE INVENTION

The human intervertebral disc is an oval to kidney bean-shaped structure of variable size depending on its location in the spine. The outer portion of the disc is known as the annulus fibrosus (or anulus fibrosus, annulus fibrosis, anulus fibrosis, or simply "the annulus"). The inner portion of the disc is known as the nucleus pulposis, or simply "the nucleus".

The annulus is made up of ten to twenty collagen fiber lamellae. The collagen fibers within a given lamella are parallel to one another. Successive lamellae are oriented in alternating directions. About 48 percent of the lamellae are incomplete, but this value varies with location and it increases with age. On average, the lamellae lie at an angle of about sixty degrees to the vertebral axis line, but this too varies with location. The orientations of the lamellae serve to control vertebral motion (i.e., one half of the bands tighten to check motion when the vertebra above or below the disc are turned in either direction).

The annulus contains the nucleus, which has a consistency generally similar to that of crabmeat. The nucleus serves to transmit and dampen axial loads. A high water content (approximately 70-80 percent) assists the nucleus in this function. The water content has a diurnal variation. The nucleus imbibes water while a person lies recumbent. Nuclear material removed from the body and placed into water will imbibe water, swelling to several times its normal size. Activity generates increased axial loads which squeeze fluid from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes, or "degenerates", with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally, disc degeneration is painless.

Premature or accelerated disc degeneration is known as degenerative disc disease. A large portion of patients suffering from chronic lower back pain are thought to have this condition. As the disc degenerates, the nucleus and annulus functions are compromised. The nucleus becomes thinner and less able to handle compressive loads. The annulus fibers become redundant as the nucleus shrinks. The redundant annular fibers are less effective in controlling vertebral motion. This disc pathology can result in: (1) bulging of the annulus into the spinal cord or nerves; (2) narrowing of the space between the vertebrae where the nerves exit; (3) tears of the annulus (both "full-thickness" and "partial-thickness" tears) as abnormal loads are transmitted to the annulus and the annulus is subjected to excessive motion between vertebrae; and (4) disc herniation or extrusion of the nucleus through complete (i.e., full-thickness) annular tears. Degenerative disc disease is frequently the cause of substantial pain for a patient.

Current surgical treatments for disc degeneration are generally "destructive", in the sense that they involve the removal or destruction of disc tissue. One group of procedures, which includes lumbar discectomy, removes the nucleus or a portion of the nucleus. A second group of procedures destroys nuclear material. This group includes Chymopapin (an enzyme) injection, laser discectomy, and thermal therapy (i.e., heat treatment to denature proteins in the nucleus). The first two groups of procedures compromise the nucleus of the treated disc. A third group of procedures, which includes spinal fusion procedures, either removes the disc or eliminates the disc's function by connecting together two or more vertebrae, e.g., by "fusing" the vertebrae together with bone. However, such spinal fusion procedures transmit additional stress to the adjacent discs, which typically results in premature degeneration of the adjacent discs. In general, the "destructive" nature of current surgical treatments for disc degeneration can provide substantial pain relief for the patient, but it can also lead to the acceleration of adjacent disc degeneration, which can result in new pain for the patient.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of implants require the removal of the degenerated disc component to allow room for the replacement prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements may cause lower back pain if too much pressure is applied to the annulus. As discussed in U.S. Pat. Nos. 6,878,167 and 7,201,774, the content of each being expressly incorporated herein by reference in their entirety, the posterior portion of the annulus has abundant pain fibers.

Herniated nucleus pulposus occurs from tears (or "fissures") in the annulus. The herniated nucleus material often applies pressure to the nerves or spinal cord. Compressed nerves can cause back and leg or arm pain. Although a patient's symptoms result primarily from the pressure caused by the herniated nucleus, the primary pathology lies in the torn annulus.

Surgery for the herniated nucleus, which is sometimes referred to as a microlumbar discectomy, only addresses the herniated nucleus. With such surgery, the surgeon removes the herniated nucleus material which is pressing on the nerves or spinal cord. In addition, in order to reduce the risk of extruding additional pieces of nucleus through the defect in the annulus, the surgeon also generally remove generous amounts of the nucleus still within the annulus. However, this generally requires that the tear or fissure in the annulus be enlarged so as to allow the surgeon access to the nucleus material still within the annulus, and this enlargement of the tear or fissure further weakens the annulus. As a result, while a microlumbar discectomy frequently decreases or eliminates a patient's back and leg or arm pain, the procedure typically further damages the already-weakened discs, which may lead to the creation of future pain for the patient.

Thus there is a need for a new and improved method and apparatus for closing fissures in the annulus.

SUMMARY OF THE INVENTION

The present invention provides a new and improved method and apparatus for closing fissures in the annulus.

More particularly, the present invention facilitates the reconstruction of the annulus and, in some cases, the nucleus as well. Such reconstruction prevents recurrent herniation following a microlumbar discectomy. The invention may also be used in the treatment of herniated discs, annular tears of the disc, or disc degeneration, while enabling surgeons to preserve the contained nucleus. The method and apparatus of the present invention may be used to treat discs throughout the spine, including the cervical, thoracic, and lumbar spines of humans and animals.

The present invention also enables surgeons to reconstruct the annulus and, if desired, to replace or augment the nucleus. Novel nucleus replacements may be added to the interior of the disc. Annulus reconstruction prevents extrusion of the nucleus replacements through fissures in the annulus. The annulus reconstruction prevents disc herniation that may cause back and leg or arm pain. The nucleus replacements may be made of natural or synthetic materials. Synthetic nucleus replacements may be made of, but are not limited to, polymers including polyurethane, silicon, hydrogel, etc., and/or other materials which may include elastomers.

Preferred embodiments of the present invention include one or more flexible longitudinal fixation components (e.g., filaments) extending across a soft tissue defect, such as a fissure in the annulus. One, two, three, four or more transverse anchor components (e.g., bar anchors), connected to the one or more flexible longitudinal fixation components, are preferably placed behind an inner layer of the annulus on opposite sides of the fissure, so as to anchor the one or more flexible longitudinal fixation components to the annulus, with the one or more flexible longitudinal fixation components extending axially through the annulus and laterally across the fissure so as to hold the fissure closed, whereby to prevent nucleus material from passing out the fissure and pressing on the adjacent nerves, including the spinal cord.

Significantly, it has been discovered that applying significant tension (e.g., about 15 N to 25 N) to the flexible longitudinal fixation components first in an axial direction substantially perpendicular to the adjacent surface of the annulus, and then in a lateral direction substantially parallel to the adjacent surface of the annulus, provides a significantly improved closure of the fissure in the annulus. More particularly, it has been discovered that applying significant tension (e.g., about 15 N to 25 N) to the flexible longitudinal fixation components first in an axial direction substantially perpendicular to the adjacent surface of the annulus pulls the transverse anchor components securely against an inner surface of the annulus, in a sort of "pre-tension" action. Thereafter, applying significant tension (e.g., about 15 N to 25 N) in a lateral direction substantially parallel to the adjacent surface of the annulus draws the fissure closed in a sort of "closing tension" action. Significantly, this serial application of a significant axial pre-tension, followed by a significant lateral closing tension, ensures a tight closure of the fissure and hence raises the pressure required to extrude nucleus material through the fissure. Prior to this discovery, flexible longitudinal fixation components were secured at a maximum of about 6 N tension, and even then in only a lateral direction substantially adjacent to the posterior surface of the annulus, which resulted in a relatively loose closure of the fissure which enabled nucleus material to extrude through the fissure. Significantly, it has now been discovered that, by increasing the tensile force applied to the flexible longitudinal fixation components to about 15 N to 25 N, and by sequentially applying the tensile force first in an axial direction substantially perpendicular to the adjacent surface of the annulus (i.e., in a pre-tension action) and thereafter in a lateral direction substantially adjacent to the posterior surface of the annulus (i.e., in a closing tension action), the efficacy of the closure is significantly increased, and the force required to extrude nucleus material through the closed fissure is significantly increased. By way of example but not limitation, it has been found that sequentially applying about 15 N to 25 N of tensile force to the flexible longitudinal fixation components, first in an axial direction substantially perpendicular to the adjacent surface of the annulus and then in a lateral direction substantially parallel to the adjacent surface of the annulus, increases by 64% the force required to extrude nucleus material through the fissure, as compared to conventional closures effected with flexible longitudinal fixation components using about 6 N of tension applied in the single, "parallel-to-the-annulus" direction of the prior art.

In one preferred form of the present invention, the flexible longitudinal fixation components (e.g., the filaments) are welded together so as to hold the fissure closed. This approach eliminates the need for knots, which inevitably slip and thereby reduce the tension across a fissure, and hence can allow nucleus material to migrate into and through the fissure. Welded flexible longitudinal fixation components are not subject to such creep or slippage and therefore maintain the desired tension across the fissure, which prevents the migration of even small amounts of nucleus material into or across the fissure.

The present invention may also be used to close other soft tissue defects in the bodies of humans or animals.

And the flexible longitudinal fixation components (e.g., the filaments) may be anchored to one of the upper and lower vertebral bodies.

In one preferred form of the present invention, there is provided a method for closing a fissure in a region of tissue having an inner surface and an outer surface, the method comprising:

providing at least a pair of transverse anchor components, each transverse anchor component being coupled to at least one flexible longitudinal fixation component having a longitudinal axis;

placing the transverse anchor components relative to the inner surface of the tissue on both sides of the fissure such that an exposed end of a flexible longitudinal fixation component extends through the tissue and past the outer surface of the tissue on both sides of the fissure;

applying axial tension to the exposed ends; and anchoring the exposed ends.

In another preferred form of the present invention, there is provided apparatus for closing a fissure in tissue, the apparatus comprising:

a filament comprising a distal end and a proximal end; and a plurality of transverse anchors slidably mounted to said filament intermediate said distal and proximal ends;

the distal end of said filament being devoid of a stop.

In another preferred form of the present invention, there is provided apparatus for closing a fissure in tissue, the apparatus comprising:

a first filament having a distal end and a proximal end;

a pair of transverse anchors linked by a second filament; and a pair of transverse anchors linked by a third filament;

said pair of transverse anchors linked by said second filament being slidably mounted to said first filament intermediate said distal and proximal ends of said first filament; and said pair of transverse anchors linked by said third filament being slidably mounted to said first filament intermediate said distal and proximal ends of said first filament.

In another preferred form of the present invention, there is provided apparatus for closing a fissure in tissue, the apparatus comprising:

a first filament having a distal end and a proximal end;

a transverse anchor attached to said distal end of said first filament; and a second filament attached to said proximal end of said first filament, said second filament being constructed to break upon the application of a predetermined amount of tension.

In another preferred form of the present invention, there is provided a method for closing a fissure in the annulus of an intervertebral disc, comprising:

providing a first transverse anchor having a first filament extending therefrom, and providing a second transverse anchor having a second filament extending therefrom;

advancing said first transverse anchor through the annulus of the intervertebral disc on one side of the fissure so that the first transverse anchor is disposed within the interior of the intervertebral disc and the first filament extends through the wall of the annulus on one side of the fissure, and advancing said second transverse anchor through the annulus of the intervertebral disc on a second side of the fissure so that the second transverse anchor is disposed within the interior of the intervertebral disc and the second filament extends through the wall of the annulus on the second side of the fissure, and applying tension to the first and second filaments so as to close the fissure; and welding the first filament to the second filament.

In another preferred form of the present invention, there is provided a construct for closing a fissure in the annulus of an intervertebral disc, comprising:

a first transverse anchor having a first filament extending therefrom, and a second transverse anchor having a second filament extending therefrom;

said first filament being welded to said second filament.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

For the purposes of clarity of description, the present invention will hereinafter generally be discussed in the context of closing a tear or fissure formed in the posterior annulus of an intervertebral disc, however, it should be appreciated that the present invention is also applicable to closing a tear or fissure formed in another portion of the annulus of an intervertebral disc, or to closing a tear or fissure or other opening formed in another anatomical structure, etc.

Figure 1A:
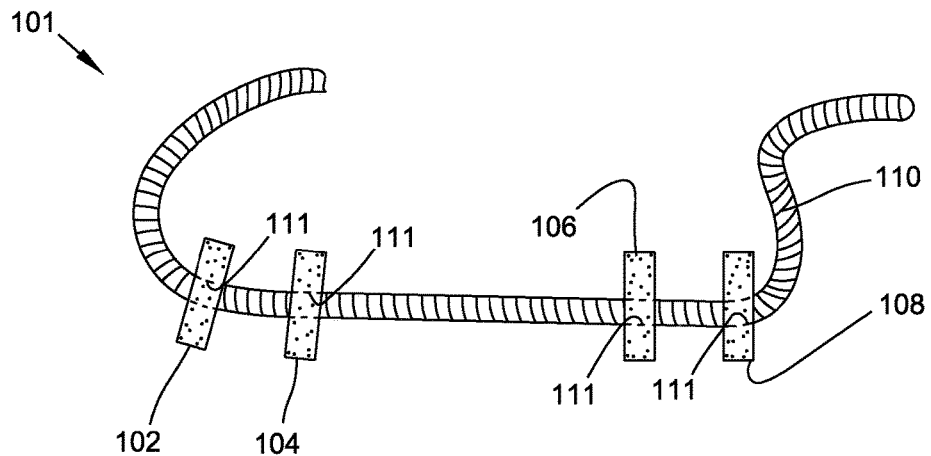
FIG. 1A is a schematic view showing one preferred form of apparatus for closing a fissure in the annulus.

FIG. 1A is a schematic view showing apparatus 101 for closing a fissure in the annulus. Apparatus 101 generally comprises cylindrical transverse anchor components (e.g., bar anchors) 102, 104, 106, 108 that are slidably mounted on a flexible longitudinal fixation component (e.g., filament) 110. The flexible longitudinal fixation component 110 passes through a hole 111 in each transverse anchor component 102, 104, 106, 108. The transverse anchor components 102, 104, 106, 108 are preferably about 0.8 to 2 millimeters in diameter, and most preferably about 1.1 to 1.3 millimeters in diameter, and about 3 to 7 millimeters in length, and most preferably about 4 to 5 millimeters in length. The holes 111 in transverse anchor components 102, 104, 106, 108 are preferably about 0.3 to 0.8 millimeters in diameter, and most preferably about 0.55 to 0.65 millimeters in diameter.

The proximal and distal portions of the holes 111 in transverse anchor components 102, 104, 106, 108 are preferably beveled, or have rounded edges, so as to reduce friction between flexible longitudinal fixation component 110 and the transverse anchor components 102, 104, 106, 108, and so as to reduce the risk of the edges of the holes 111 cutting the flexible longitudinal fixation component 110. The transverse anchor components 102, 104, 106, 108 are preferably cylindrical, but may be elongate with a non-circular cross-section in alternative embodiments of the invention. For example, such transverse anchor components 102, 104, 106, 108 may have triangular, square, hexagonal or other shapes in cross-section. Two or more transverse anchor components 102, 104, 106, 108 (e.g., 4 to 8 such transverse anchor components) may be provided for each flexible longitudinal fixation component 110 in alternative embodiments of the invention.

The transverse anchor components 102, 104, 106, 108 may be made of titanium, tantalum, stainless steel, polypropylene, Delrin, polyetheretherketone (PEEK), or any other suitable material. By way of example but not limitation, the transverse anchor components 102, 104, 106, 108 may be made of molded PEEK.

The flexible longitudinal fixation component 110 is preferably formed out of weldable suture, e.g., size 2-0 to #4 non-absorbable suture, and most preferably size #2 or #3 weldable suture. By way of example but not limitation, the flexible longitudinal fixation component 110 may be made of size #2 bicomposite braided polyester weldable suture of the type provided by Tornier (Edina, Minn.). The flexible longitudinal fixation component 110 is preferably about 40 to 120 centimeters long, and most preferably about 70 to 95 centimeters long.

Figure 1B:
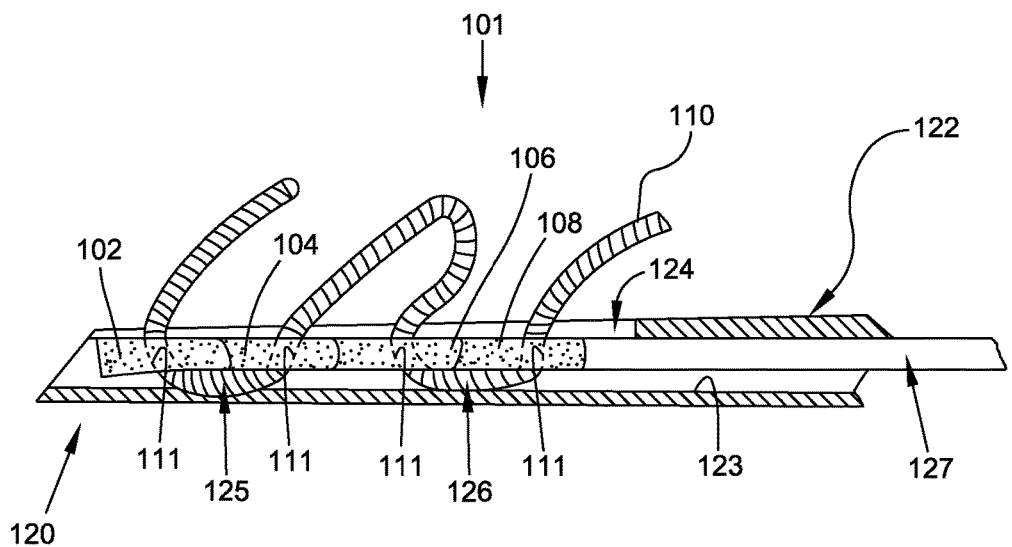
FIG. 1B is a schematic view showing the apparatus of FIG. 1A loaded in the distal end of a needle-like insertion device.

FIG. 1B is a schematic view showing apparatus 101 loaded in the distal end 120 of a needle-like insertion device 122. The longitudinal axes of the transverse anchor components 102, 104, 106, 108, which are co-linear and most preferably co-axial with one another, are seen loaded in the distal end of the lumen 123 of needle-like insertion device 122. Such needle-like insertion device 122 is described and illustrated in the aforementioned U.S. patent application Ser. No. 12/263,753 and 61/414,186, both of which are incorporated herein by reference. The ends and the central portion of the flexible longitudinal fixation component 110 extend out through a slot 124 formed in the side of the distal end 120 of the needle-like insertion device 122. The central portion of the flexible longitudinal fixation component 110 (i.e., the portion which extends through the slot 124 in the needle-like insertion device 122) is preferably about 10 to 30 millimeters long. The slot 124 in the side of the distal end 120 of the needle-like insertion device 122 is preferably about 1 to 6 centimeters long or longer, and most preferably about 2 to 4 centimeters long. The slot 124 is preferably about 0.8 to 2.0 millimeters wide, and most preferably about 1 millimeter wide. The two portions 125, 126 (FIG. 1B) of the flexible longitudinal fixation component 110 that extend between the first and second transverse anchor components 102, 104 and the third and fourth transverse anchor components 106, 108, respectively, are seen in FIG. 1B residing between the transverse anchor components 102, 104, 106, 108 and the side wall of the lumen 123 of needle-like insertion device 122.

Figure 1C:
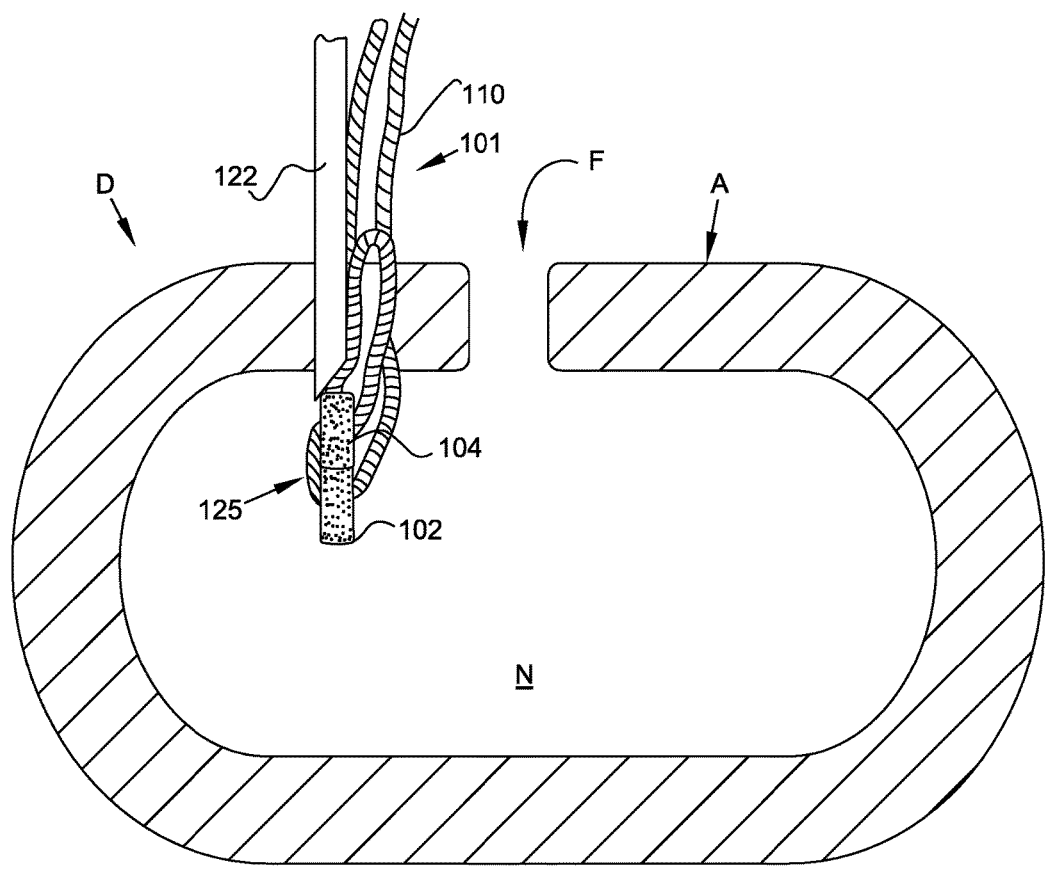
FIG. 1C is a schematic view showing the apparatus of FIG. 1B penetrating the annulus of an intervertebral disc on one side of a fissure.

FIG. 1C is a schematic view showing needle-like insertion device 122 advancing a portion of the apparatus 101 through the annulus A of the intervertebral disc D on one side of a tear or fissure F and into the nucleus N. A stylet component 127 (FIG. 1B) slidably disposed in the lumen 123 of the needle-like insertion device 122 forces the first and second transverse anchor components 102, 104 out of the distal end of the needle-like insertion device 122 after the distal end of the needle-like insertion device 122 has passed through the annulus A on a first side of a fissure F in the annulus. The ends and central portion of the flexible longitudinal fixation component 110 are seen extending through the hole in the posterior annulus created by passage of the needle-like insertion device 122. Note that when the first and second transverse anchor components 102, 104 are ejected from the distal end of the needle-like insertion device 122 into the nucleus N of the intervertebral disc D, the distal end of the needle-like insertion device 122 must have been advanced a sufficient distance into the nucleus N for the first and second transverse anchor components 102, 104 to be able to turn (i.e., from the longitudinal orientation of FIG. 1C to the transverse orientation of FIGS. 1D, 1E and 1F) so as to prevent the first and second transverse anchor components 102, 104 from being pulled back through the posterior annulus. Note also that at this level of penetration into the nucleus N, a substantial amount of nucleus material will be interposed between the first and second transverse anchor components 102, 104 and the inner surface of the posterior annulus.

Figure 1D:
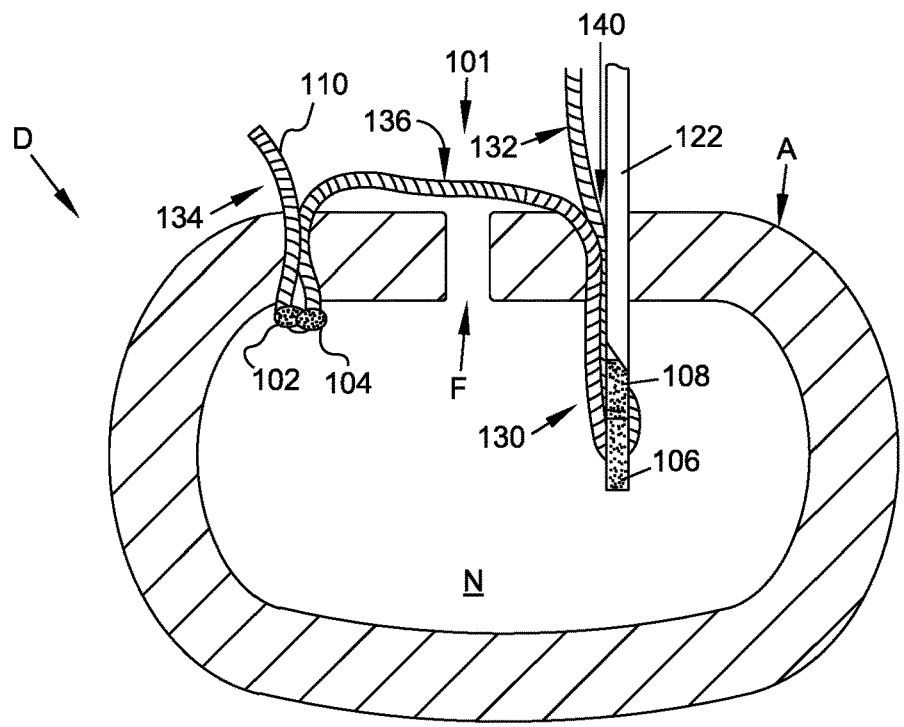
FIG. 1D is a schematic view like that of FIG. 1C, but showing the apparatus of FIG. 1B penetrating the annulus on a second side of the fissure.

FIG. 1D is a schematic view showing the apparatus 101 and the needle-like insertion device 122 penetrating the annulus A on a second side of the fissure F. More particularly, at this point in the procedure, axial tension has been applied to the distal end of the flexible longitudinal fixation component 110 so as to pull the first and second transverse anchor components 102, 104 back against the inner surface of the posterior annulus. This may be done by pulling on the flexible longitudinal fixation component 110 on both sides of the first and second transverse anchor components 102, 104 in a direction perpendicular to the posterior wall of the annulus with a force of about 15 N to 25 N so as to pull the first and second transverse anchor components 102, 104 back through the intervening nucleus material so that the first and second transverse anchor components 102, 104 seat securely against the inner surface of the posterior annulus. It has been found that a force of this direction and magnitude is needed to reliably move the first and second transverse anchor components 102, 104 through the heavy crabmeat-like consistency of the nucleus N. In addition, the stylet component 127 in the lumen 123 of the needle-like insertion device 122 forces the third and fourth transverse anchor components 106, 108 from the distal end of the needle-like insertion device 122 after the distal end of the needle-like insertion device 122 has passed through the posterior annulus on a second side of the fissure F, which is generally opposite to the side on which the previously-inserted transverse anchor components 102, 104 were set. It will be appreciated that as this occurs, a length of the flexible longitudinal fixation component 110 will extend laterally across the fissure F.

In FIG. 1D, the proximal end 132 and central portion 130 of the flexible longitudinal fixation component 110 are seen extending axially through the hole 140 formed in the annulus A by the needle-like insertion device 122. The distal 5 to 25 millimeters of the needle-like insertion device 122 may preferably be curved in alternative embodiments of the invention. Again, when the third and fourth transverse anchor components 106, 108 are ejected from the distal end of the needle-like insertion device 122 into the nucleus N, the distal end of the needle-like insertion device 122 must have been advanced a sufficient distance into the nucleus N for the third and fourth transverse anchor components 106, 108 to be able to turn (i.e., from the longitudinal orientation of FIG. 1D to the transverse orientation of FIGS. 1E and 1F) so as to prevent the third and fourth transverse anchor components 106, 108 from being pulled back through the annulus. Note also that at this level of penetration into the nucleus, a substantial amount of nucleus material will be interposed between the third and fourth transverse anchor components 106, 108 and the inner surface of the posterior annulus. Again, axial tension is applied to the flexible longitudinal fixation component 110 to pull the third and fourth transverse anchor components 106, 108 back against the inner surface of the posterior annulus. This may be done by pulling on the flexible longitudinal fixation component 110 on both sides of the third and fourth transverse anchor components 106, 108 in a direction perpendicular to the posterior wall of the annulus with a force of about 15 N to 25 N so as to pull the third and fourth transverse anchor components 106, 108 back through the intervening nucleus material so that the third and fourth transverse anchor components 106, 108 seat securely against the inner surface of the posterior annulus. Again, it has been found that a force of this direction and magnitude is needed to reliably move the third and fourth transverse anchor components 106, 108 through the heavy, crabmeat-like consistency of the nucleus N.

Thus it will be seen that axial tension applied to the distal end 134 of the flexible longitudinal fixation component 110 and the central portion 136 of the flexible longitudinal fixation component 110 pulls the first and second transverse anchor components 102, 104 against the inner surface of the posterior annulus, and axial tension applied to the proximal end 132 of the flexible longitudinal fixation component 110 and the central portion 136 of the flexible longitudinal fixation component 110 pulls the third and fourth transverse anchor components 106, 108 against the inner surface of the posterior annulus. Again, this tension should be applied axially (i.e., substantially perpendicular to the posterior wall of the annulus), and at a substantial level (e.g., at about 15 N to 25 N), in order to ensure proper seating of the transverse anchor components 102, 104, 106, 108 against the inner surface of the posterior annulus. Once the transverse anchor components 102, 104, and the transverse anchor components 106, 108, have been properly seated against the inner surface of the posterior annulus (i.e., once the transverse anchor components 102, 104, 106, 108 have been "pre-tensioned"), the distal and proximal ends 134, 132 of the flexible longitudinal fixation component 110 may be drawn together (e.g., with a lateral force of about 15 N to 25 N, directed substantially parallel to the posterior wall of the annulus) so as to draw the fissure F closed, and then the distal and proximal ends 134, 132 of the flexible longitudinal fixation component 110 may be locked together as shown in FIG. 1E.

Figure 1E:
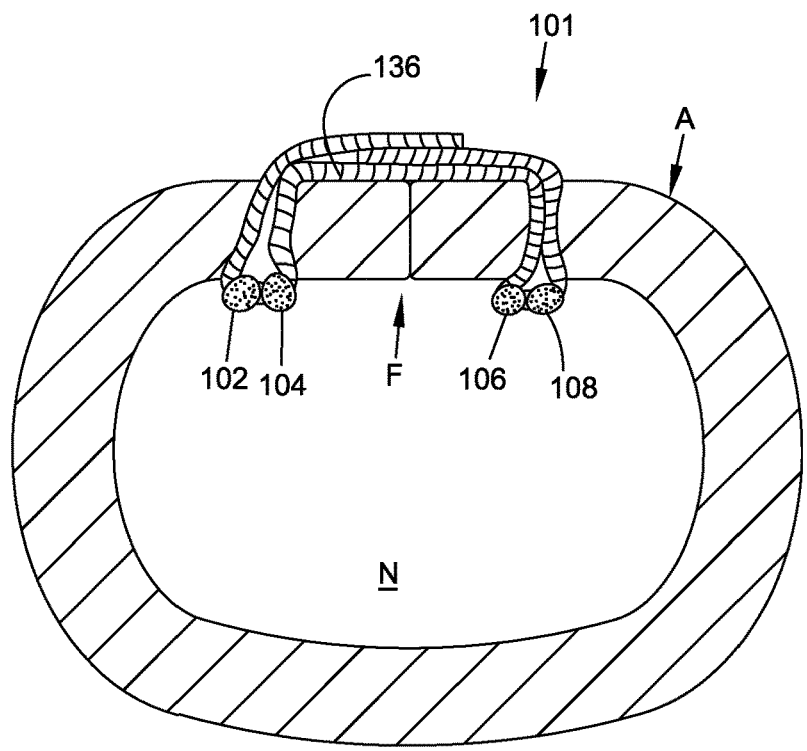
FIG. 1E is a schematic view showing the apparatus of FIG. 1A closing the fissure in the annulus.

More particularly, FIG. 1E is a schematic view showing how tension (e.g., about 15 N to 25 N) applied laterally to the distal and proximal ends 134, 132 of the flexible longitudinal fixation component 110 tightens the central portion 136 of the flexible longitudinal fixation component 110, which extends laterally over the fissure or defect F in the annulus. The distal and proximal ends 134, 132 of the flexible longitudinal fixation component 110 are fastened or locked together, preferably by welding under tension, so as to reduce the width of the fissure F. For example, the thermal welder provided by Tornier (Edina, Minn.) may be used to apply about 16 N of lateral tension on the ends 134, 132 of the flexible longitudinal fixation component 110 and then weld the ends 134, 132 to each other so as to make the fixation secure. Alternatively, the ends 134, 132 of the flexible longitudinal fixation component 110 could be welded together under about 10 N to 25 N of tension, or more, in alternative embodiments of the invention. Alternatively, pre-tied knots or other fastening methods or devices may be used to lock the distal and proximal ends 134, 132 of the flexible longitudinal fixation component 110 together in alternative embodiments of the invention.

Again, as described above in connection with the description of FIGS. 1D and 1E, substantial (e.g., about 15 N to 25 N) axial (i.e., substantially perpendicular to the posterior wall of the annulus) tension is applied to the distal end 134 and central portion 136 of the flexible longitudinal fixation component 110 so as to pull the first and second transverse anchor components 102, 104 against the inner surface of the posterior annulus, and substantial (e.g., about 15 N to 25 N) axial (e.g., substantially perpendicular to the posterior wall of the annulus) tension is applied to the proximal end 132 and central portion 136 of the flexible longitudinal fixation component 110 so as to pull the third and fourth transverse anchor components 106, 108 against the inner surface of the posterior annulus, before the distal and proximal ends 134, 132 of the flexible longitudinal fixation component 110 are pulled laterally (i.e., in a direction substantially parallel to the posterior wall of the annulus) under substantial (e.g., about 15 N to 25 N) tension so as to close the fissure F, whereupon the two ends 134, 132 of the flexible longitudinal fixation component 110 are welded or otherwise locked together.

Thus it will be seen that, with the present invention, a filament (e.g., the flexible longitudinal fixation component 110) is used to laterally span a tear, fissure or other defect in the annulus, with one portion of the filament being anchored to the annulus by passing at least one first anchor (e.g., a transverse anchor component) through the annulus and into the nucleus on one side of the fissure, and with a second portion of the filament being anchored to the annulus by passing at least one second anchor (e.g., a transverse anchor component) through the annulus and into the nucleus on a second side of the fissure, with the at least one first and second anchors being drawn back through the nucleus and against the inner surface of the posterior annulus by the application of a significant (e.g., about 15 N to 25 N) axial tension applied perpendicular to the posterior wall of the annulus (i.e., by a "pre-tension"), and with the fissure being drawn closed by the subsequent application of a significant (e.g., about 15 N to 25 N) lateral tension applied parallel to the posterior wall of the annulus (i.e., by a "closing tension"), and with the free ends of the filament thereafter being secured to one another (e.g., by welding) so as to hold the fissure closed.

Figure 1F:
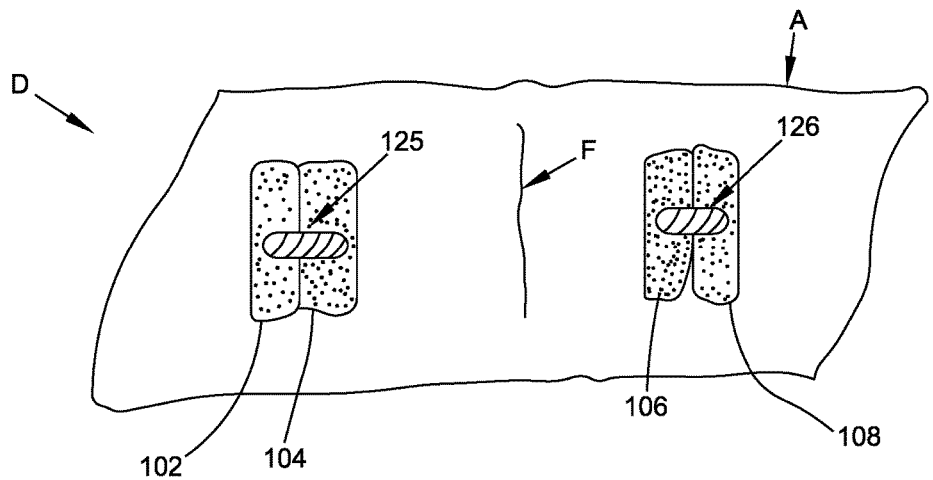
FIG. 1F is a schematic view showing the apparatus of FIG. 1A disposed against the inner surface of the annulus.

FIG. 1F is a schematic view showing the inner surface of the posterior annulus, with two or more transverse anchor components disposed on each side of the fissure F so as to increase the area of contact between the transverse anchor components and the inner surface of the posterior annulus, as compared to a single anchor component having the same diameter as the transverse anchor components described above, which increases the force required to pull the transverse anchor components through the annulus, which can be weakened from previous tears. Deploying multiple transverse anchor components on each side of the fissure F also increases the radius of curvature of the portions of the flexible longitudinal fixation component 110 where such component passes through the transverse anchor components, compared to a single transverse anchor component on either side, which reduces the friction between the flexible longitudinal fixation component 110 and the transverse anchor components, and hence facilitates tightening of the flexible longitudinal fixation component 110.

Figure 1G:
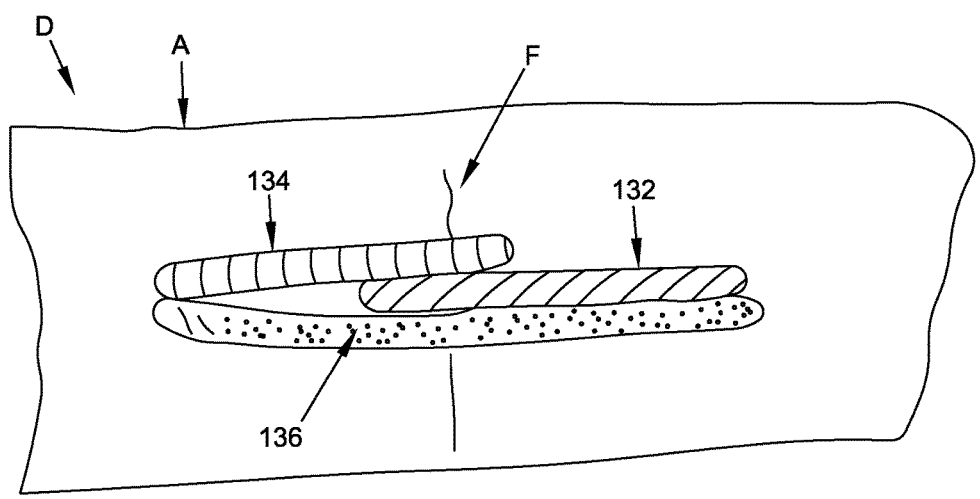
FIG. 1G is a schematic view showing the apparatus of FIG. 1A disposed against the outer surface of the annulus.

FIG. 1G is a schematic view showing the outer layer of the posterior annulus and the flexible longitudinal fixation component 110 welded in position. The width of the flexible longitudinal fixation component 110, which is preferably about 0.5 millimeters wide, is effectively tripled to 1.5 millimeters total width when welded together so as to form a wide barrier to resist nucleus extrusion through the closed fissure F. High tension on the flexible longitudinal fixation component 110 also creates a stiff construct spanning the fissure F, which resists pressure from the nucleus N trying to extrude through the closed fissure F. The ends 134, 132 of the flexible longitudinal fixation component 110 are welded together in side-by-side relation, and the welded portion of the flexible longitudinal fixation component 110 lies beside the central portion 136 of the flexible longitudinal fixation component 110, whereby to minimize construct thickness and hence decrease the risk of nerve compression or nerve irritation by the construct.

Figure 2A:
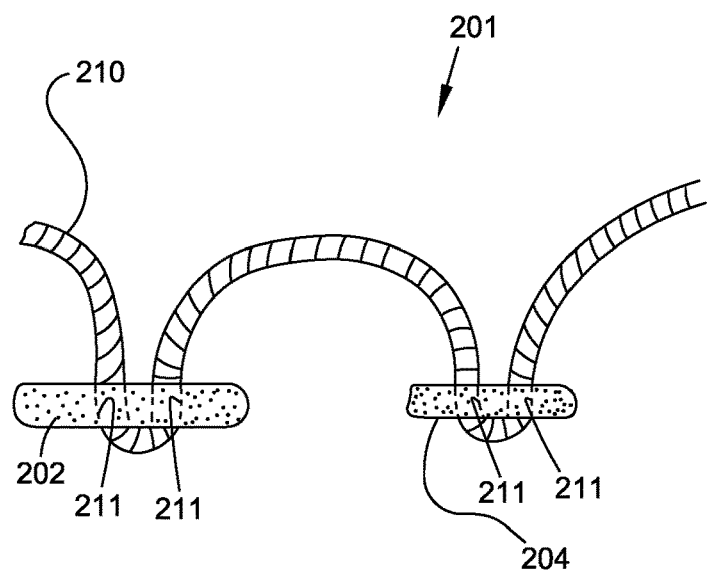
FIG. 2A is a schematic view showing another preferred form of apparatus for closing a fissure in the annulus.

FIG. 2A is a schematic view showing an alternative form of the present invention. More particularly, FIG. 2A shows apparatus 201 where the flexible longitudinal fixation component 210 passes through two holes 211 formed in each of the two transverse anchor components 202, 204. The edges of the holes 211 are preferably about 0.5 to 2 millimeters apart, and most preferably about 1 millimeter apart. The various components of apparatus 201 are preferably about the same size as their counterpart components of the aforementioned apparatus 101 and are preferably made out of the same or similar materials.

Figure 2B:
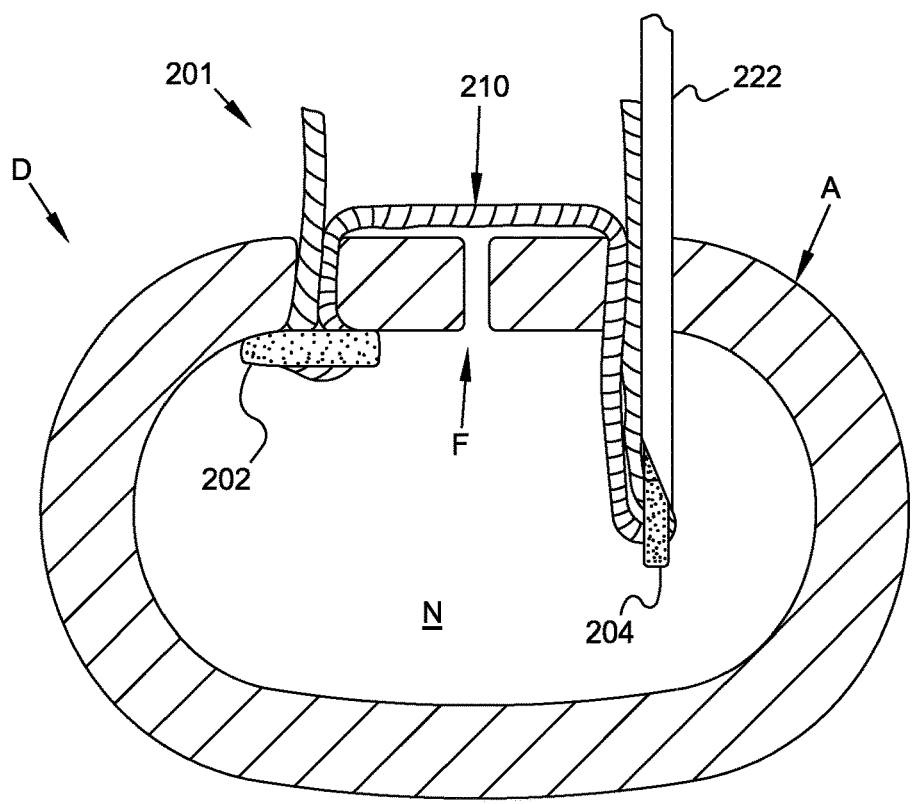
FIG. 2B is a schematic view showing the apparatus of FIG. 2A and a needle-like insertion device penetrating the annulus on first and second sides of a fissure.

FIG. 2B is a schematic view showing the apparatus 201 being installed in an intervertebral disc D so as to close a tear or fissure F in the annulus A, whereby to prevent the extrusion of the nucleus N. More particularly, first transverse anchor component 202 is inserted through a first side of the annulus A (i.e., using needle-like insertion device 222), and then significant (e.g., about 15 N to 25 N) axial (i.e., applied perpendicular to the posterior wall of the annulus) tension is applied on the distal end of the flexible longitudinal fixation component 210 so as to pull the first transverse anchor component 202 through the intervening layers of nucleus N and seat it against the inner layer of the posterior annulus. FIG. 2A also shows the second transverse anchor component 204 being pushed from the insertion device 222 (e.g., with a stylet), which was passed through a second side of the annulus, so as to deposit second transverse anchor component 204 intermediate the nucleus N.

Figure 2C:
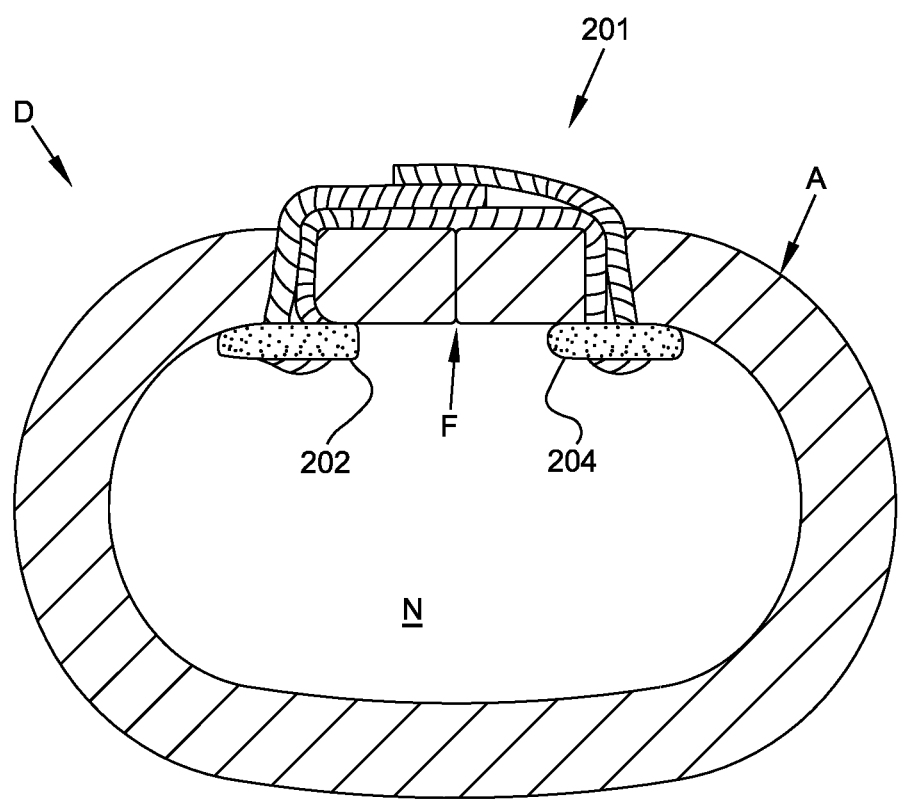
FIG. 2C is a schematic view showing the apparatus of FIG. 2A closing the fissure in the annulus.

FIG. 2C is a schematic view showing apparatus 201 secured in position so as to close the fissure F in the annulus A. More particularly, after each of the transverse anchor components 202, 204 is passed through the annulus using needle-like insertion device 222 and ejected from the needle-like insertion device 222 into the midst of the nucleus N, a significant (e.g., about 15 N to 25 N) axial (i.e., applied perpendicular to the posterior wall of the annulus) tension is applied to the ends of the flexible longitudinal fixation component 210 so as to seat (i.e., pre-tension) each of the transverse anchor components 202, 204 against the inner surface of the posterior annulus, then significant (e.g., about 15 N to 25 N) lateral (i.e., applied in a direction substantially parallel to the posterior wall of the annulus) tension is applied to the two ends of the flexible longitudinal fixation component 210 so as to draw the fissure F closed (i.e., with closing tension), and then the two free ends of the flexible longitudinal fixation component 210 are welded together so as to secure apparatus 201 in the position shown in FIG. 2C.

Figure 2D:
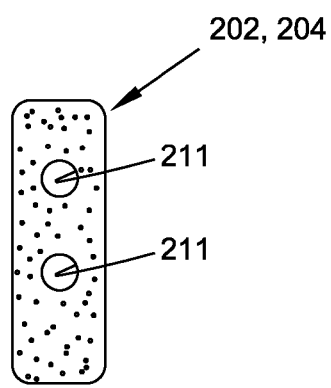
FIG. 2D is a schematic view showing one possible form of transverse anchor component of the apparatus of FIG. 2A.

FIG. 2D is a schematic view showing a transverse anchor component 202, 204 including the holes 211 for receiving the flexible longitudinal fixation component 210.

Figure 2E:
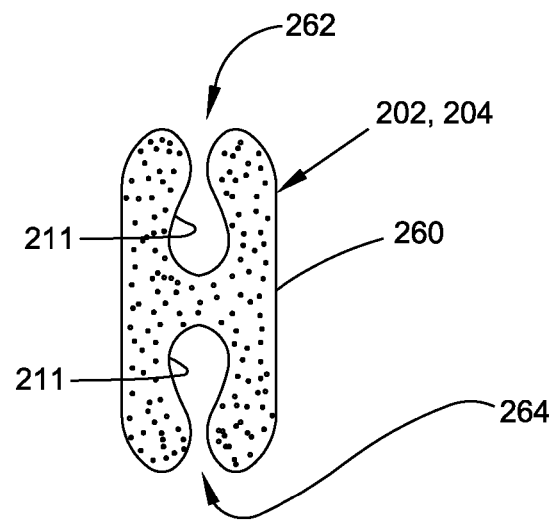
FIG. 2E is a schematic view showing another possible form of transverse anchor component of the apparatus of FIG. 2A.

FIG. 2E is a schematic view showing an alternative transverse anchor component 202, 204. In this form of the invention, slots 262, 264 extend between holes 211 and the longitudinal ends of the transverse anchor component 202, 204. With this construction, the flexible longitudinal fixation component 210 is pushed thorough slots 262, 264 in the ends of the transverse anchor component 202, 204 so as to seat the flexible longitudinal fixation component 210 in the holes 211. The central transverse, axle-like portion 260 of the transverse anchor component 202, 204 is preferably cylindrical in shape.

Figure 3A:
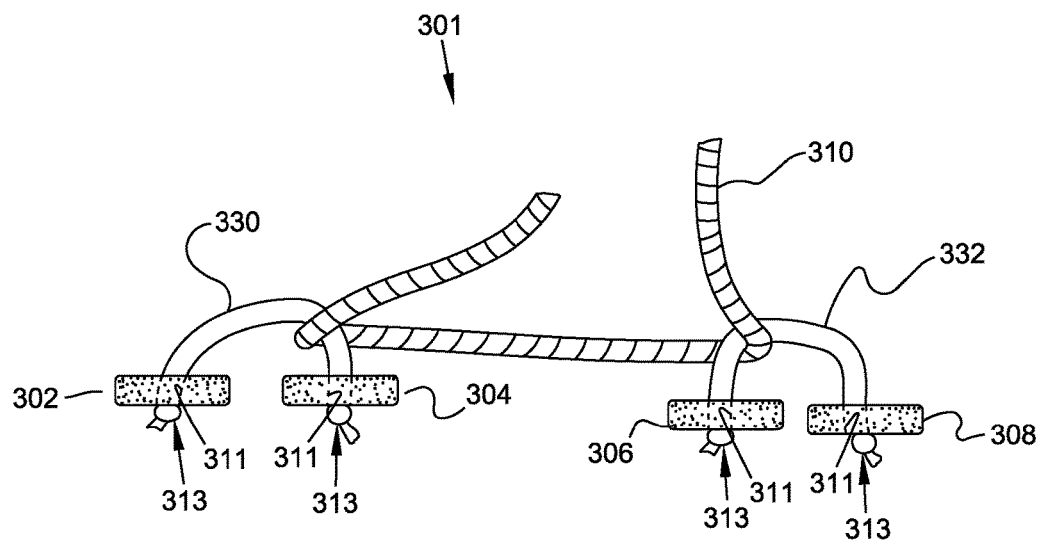
FIG. 3A is a schematic view showing another preferred form of apparatus for closing a fissure in the annulus.

FIG. 3A is a schematic view showing another form of the present invention. More particularly, FIG. 3A shows apparatus 301 comprising two smaller flexible longitudinal fixation components 330, 332 passed through holes 311 in the transverse anchor components 302, 304, 306, 308 and then knotted (e.g., at 313). The smaller flexible longitudinal fixation components 330, 332 are preferably size 2-0 to #3 non-absorbable suture. For example, the smaller flexible longitudinal fixation components 330, 332 could be made of size #2 braided polyester suture. The smaller flexible longitudinal fixation components 330, 332 are preferably about 10 to 20 millimeters long, and most preferably about 16 millimeters long. The ends of a longer flexible longitudinal fixation component 310, similar in size to the previously-described flexible longitudinal fixation components 110 and 210, and made of similar materials, are passed through the loops formed by the smaller flexible longitudinal fixation components 330, 332.

Figure 3B:
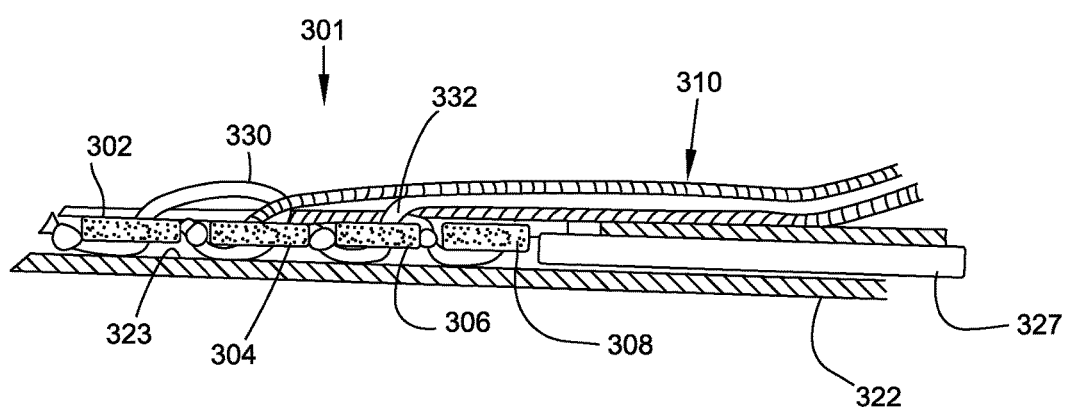
FIG. 3B is a schematic view showing the apparatus of FIG. 3A loaded in the distal end of a needle-like insertion device.

FIG. 3B is a schematic view showing apparatus 301 loaded into a needle-like insertion device 322. Again, transverse anchor components 302, 304, 306, 308 are shown disposed in the lumen 323 of the needle-like insertion device 322, with a stylus 327 being provided to selectively eject transverse anchor components 302, 304, 306, 308 from the distal end of the needle-like insertion device 322.

Figure 3C:
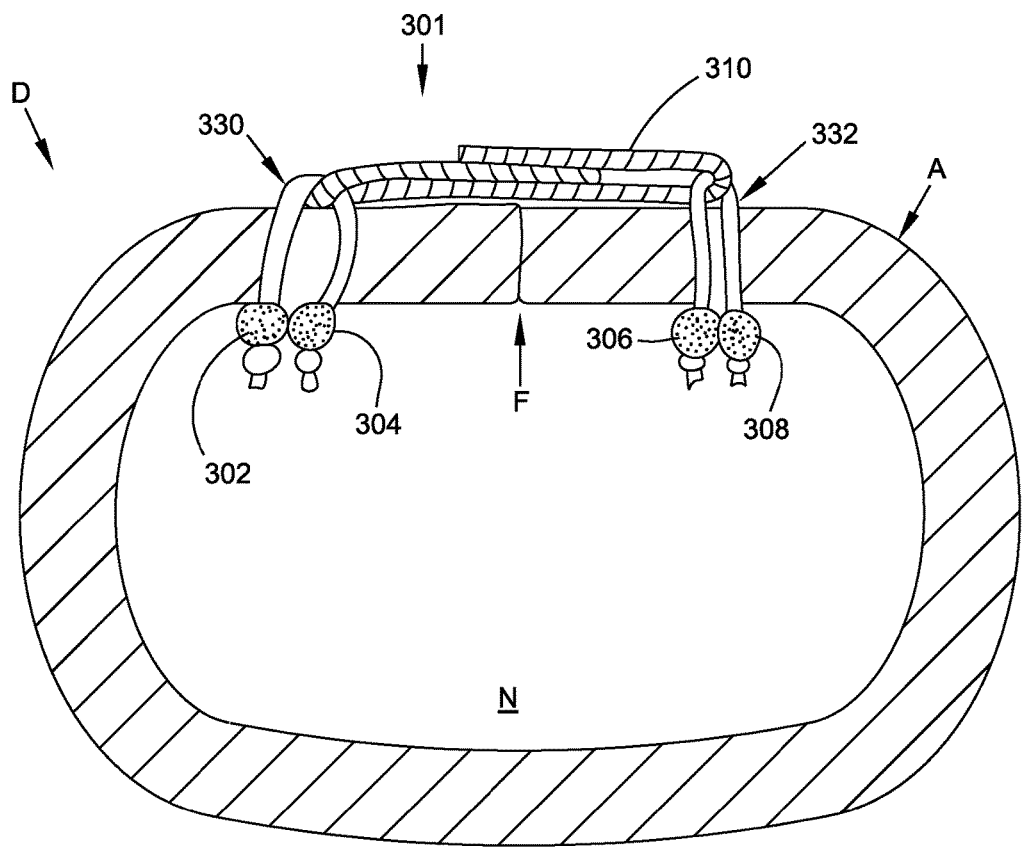
FIG. 3C is a schematic view showing the apparatus of FIG. 3A closing the fissure in the annulus.

FIG. 3C is a schematic view showing apparatus 301 installed across a fissure F in the annulus A of an intervertebral disc D so as to prevent the extrusion of nucleus N. In accordance with the present invention, needle-like insertion device 322 is used to insert the first and second transverse anchor components 302, 304 through the annulus on one side of the fissure F so that the first and second transverse anchor components 302, 304 are deployed intermediate the nucleus, and then significant (e.g., about 15 N to 25 N) axial (i.e., perpendicular to the posterior wall of the annulus) tension is applied to smaller flexible longitudinal fixation component 330 so as to seat the first and second transverse anchor components 302, 304 against the inner surface of the posterior annulus; needle-like insertion device 322 is used to insert the third and fourth transverse anchor components 306, 308 through the annulus on the other side of the fissure F so that the third and fourth transverse anchor components 306, 308 are deployed intermediate the nucleus N, and then significant (e.g., about 15 N to 25 N) axial (i.e., perpendicular to the posterior wall of the annulus) tension is applied to smaller flexible longitudinal fixation component 332 so as to seat the third and fourth transverse anchor components 306, 308 against the inner surface of the posterior annulus; then significant (e.g., about 15 N to 25 N) lateral (i.e., parallel to the posterior wall of the annulus) tension is applied to the ends of the longer flexible longitudinal fixation component 310 so as to draw the fissure F closed; and then the two free ends of the flexible longitudinal fixation component 310 are welded together. Thus, the apparatus 301 of FIGS. 3A-3C is again set using an axial pre-tension force to seat first and second transverse anchor components 302, 304, and third and fourth transverse anchor components 306, 308, against the inner layer of the posterior annulus, and then a lateral closing tension is applied to flexible longitudinal fixation component 310 so as to close the fissure F, whereupon the flexible longitudinal fixation component 310 is welded in position.

Figure 4A:
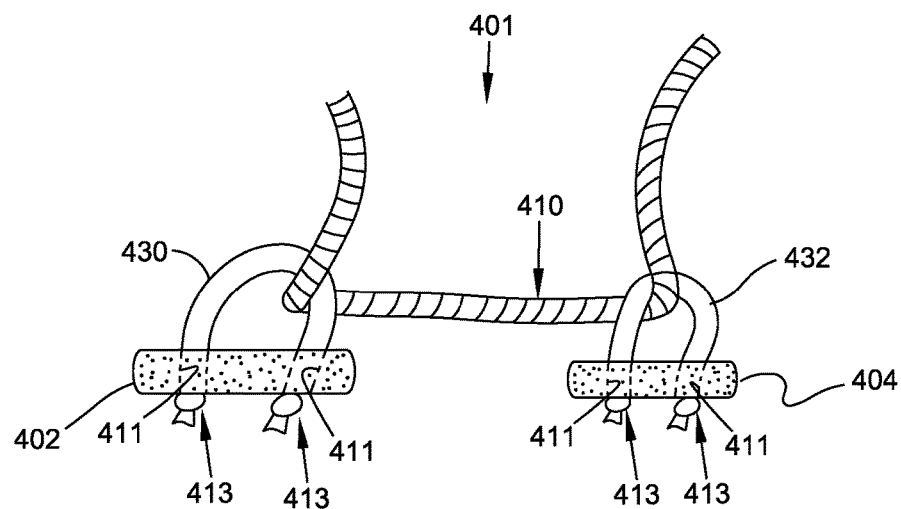
FIG. 4A is a schematic view showing another preferred form of apparatus for closing a fissure in the annulus.

FIG. 4A is a schematic view of another form of the present invention. More particularly, in FIG. 4A there is shown apparatus 401 wherein the ends the smaller flexible longitudinal fixation components 430, 432 are passed through two holes 411 in each transverse anchor component 402, 404, and then knotted (e.g., at 413). The smaller flexible longitudinal fixation components 430, 432 are preferably about 4 to 16 millimeters long, and most preferably about 6 to 12 millimeters long. The smaller flexible longitudinal fixation components 430, 432, and/or the longer flexible longitudinal fixation component 410, are preferably coated with material, such as wax or paraffin, so as to decrease friction between the flexible longitudinal fixation components 430, 432 and 410 as they slide across each other. Alternative anti-friction materials may be applied to, or incorporated in, the flexible longitudinal fixation components 430, 432 and/or 410 in alternative embodiments of the invention. Apparatus 401 is applied to an intervertebral disc D using the methods described above with respect to apparatus 301 so as to close a fissure F in the disc and thereby prevent the extrusion of nucleus N from the disc.

Figure 4B:
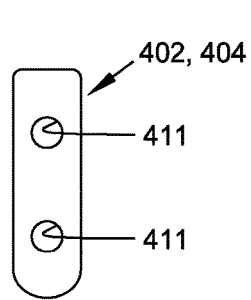
FIG. 4B is a schematic view showing one possible form of transverse anchor component of the apparatus of FIG. 4A.

FIG. 4B is a schematic view showing a transverse anchor component 402, 404 including the holes 411 for receiving the smaller flexible longitudinal fixation component 430, 432. The transverse anchor component 402, 404 is preferably similar in size and shape to the transverse anchor components 202, 204 described above with respect to fixation device 201, and is preferably formed out of the same or similar materials.

Figure 4C:
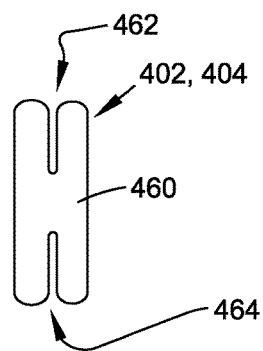
FIG. 4C is a schematic view showing another possible form of transverse anchor component of the apparatus of FIG. 4A.

FIG. 4C is a schematic view showing an alternative transverse anchor component 402, 404. In this form of the invention, slots 462, 464 extend into the distal ends of transverse anchor components 402, 404. With this construction, the ends of the smaller flexible longitudinal fixation components 430, 432 are cleated or press fit into slots 462, 464 so as to secure the smaller flexible longitudinal fixation components 430, 432 to anchor components 402, 404. Preferably the central transverse, axle-like portion 460 of the transverse anchor components 402, 404 is cylindrical in configuration.

Figure 4D:
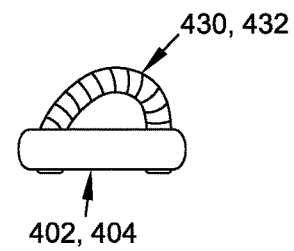
FIG. 4D is a schematic view showing the transverse anchor component of FIG. 4C, and also including a smaller flexible longitudinal fixation component (e.g., filament) attached to the transverse anchor component.

FIG. 4D is a schematic view of the construction shown in FIG. 4C, but also showing the ends of the smaller flexible fixation components 430, 432 cleated to the ends of the transverse anchor component 402, 404. Two or more (e.g., 2, 3, 4, 5, etc.) such transverse anchor components 402, 404 (with connecting smaller flexible fixation components 430, 432) could be used for each longer flexible longitudinal fixation component 410, in a manner similar to the method and apparatus shown in FIGS. 1A-1G. It should be appreciated that in this form of the invention, the distal ends of the smaller flexible longitudinal fixation components 430, 432 extend a shorter distance beyond the edge of the transverse anchor components 430, 432 than the knots 413 of the construction shown in FIG. 4A. Such a "low-profile" construction facilitates inserting and seating the transverse anchor components 402, 404 into the lumen of the associated needle-like insertion device and decreases the risk of the insertion device cutting the distal ends of the smaller flexible longitudinal fixation components 430, 432 during such loading procedure. The transverse anchor components 402, 404, with solid central sections 460, are also less likely to break than, for example, the anchor components shown in FIGS. 1A-1G and FIGS. 3A-3C.

Figure 5A:
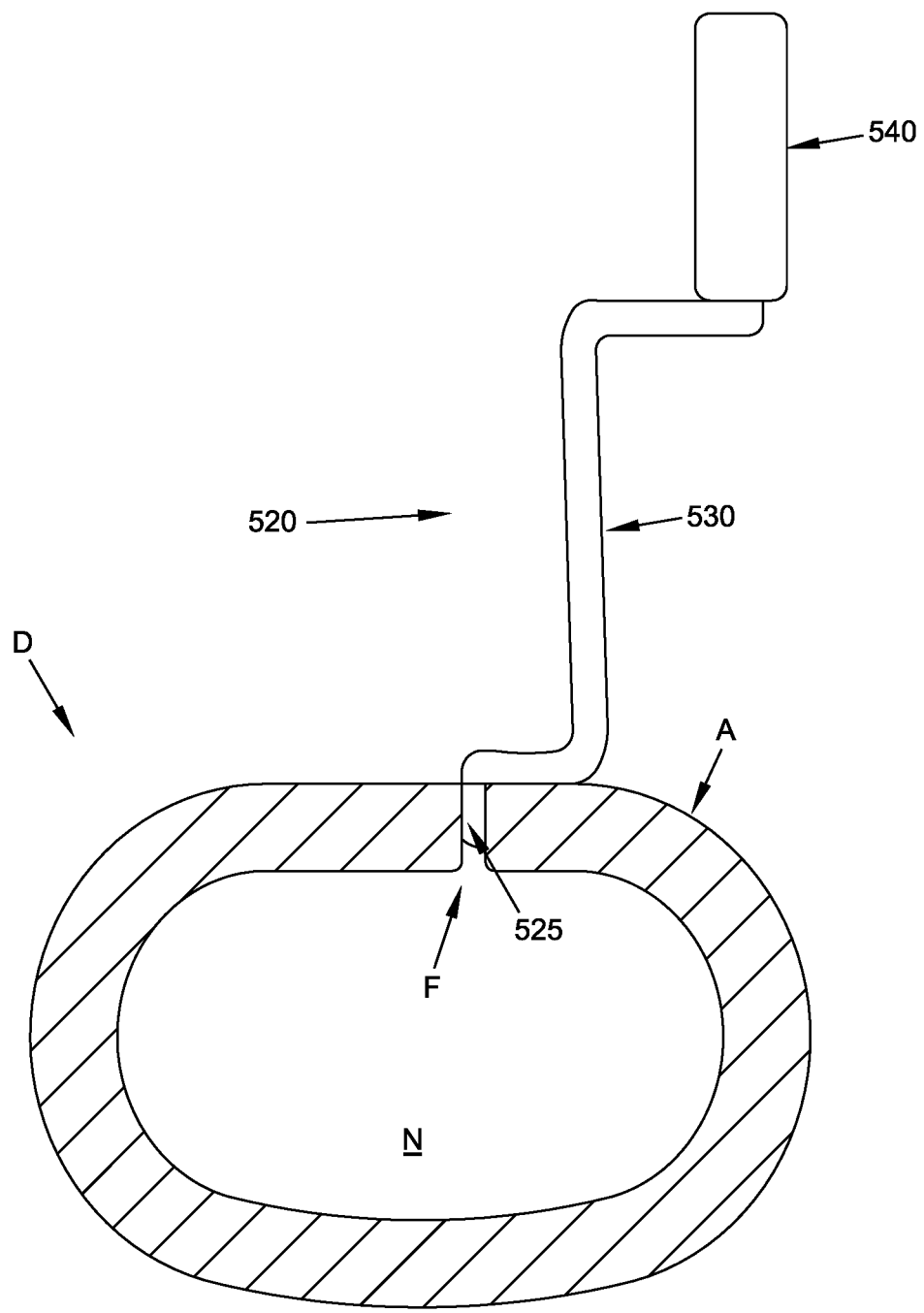
FIG. 5A is a schematic view showing a guide tool for use in closing a fissure in the annulus.
Figure 5B:
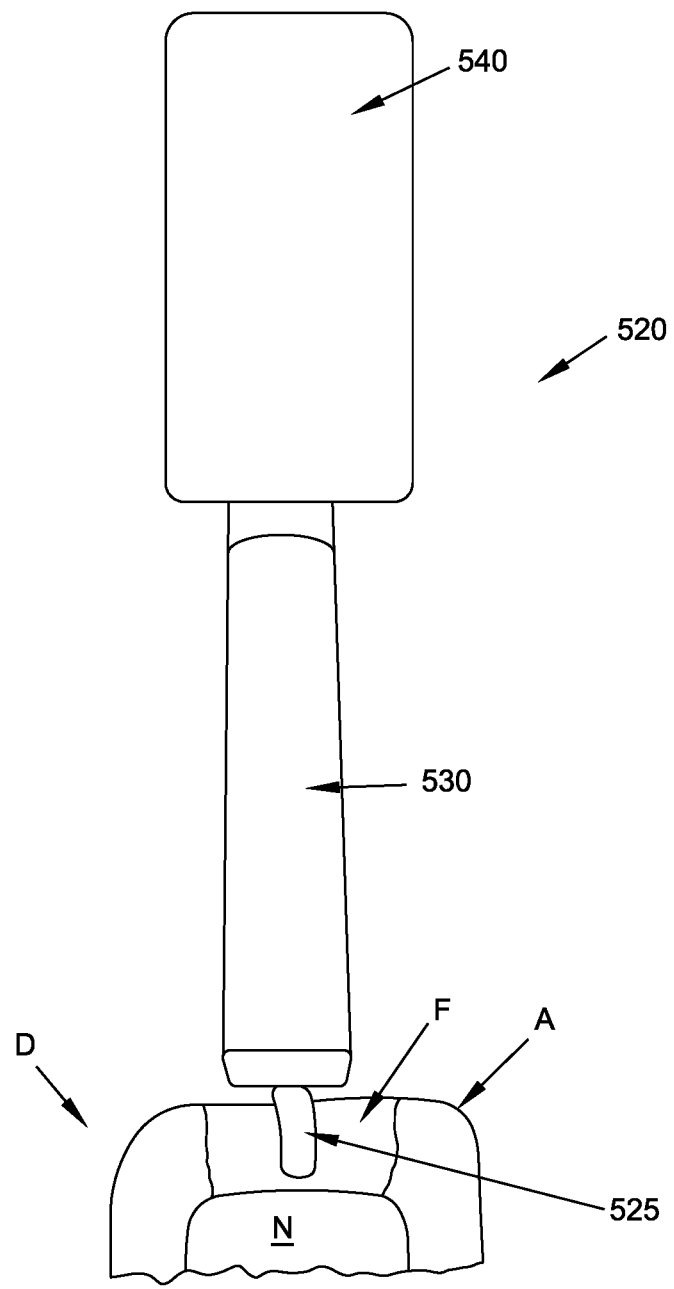
FIG. 5B is another schematic view of the guide tool of FIG. 5A.

FIGS. 5A and 5B are schematic views showing the distal end of a guide tool 520 disposed in a fissure F in the annulus A of an intervertebral disc D. Surgeons may use the guide tool 520 to identify the location of the fissure F while deploying the closure apparatus of the present invention (e.g., apparatus 101, 201, 301, 401, etc.) through the annulus. More particularly, the transverse anchor components on the first end of the closure apparatus (e.g., transverse anchor components 102, 104 of apparatus 101) are placed through the annulus approximately 2 to 6 millimeters lateral to the distal end 525 of the guide tool 520. The guide tool 520 is then rotated 180 degrees before placing the transverse anchor components on the second end of the closure apparatus (e.g., transverse anchor components 106, 108 of apparatus 101) through the annulus on the second side of the fissure. The distal end 525 of the guide tool 520 is blunt and preferably about 1 to 4 millimeters wide, about 1 to 2 millimeters thick, and about 2 to 7 millimeters long. Guide tools with smaller or larger distal tips may also be provided. The small size of the distal tip 525 of the guide tool 520 prevents annulus injury as that portion of the guide tool is pushed into the fissure. The guide tool 520 helps surgeons optimize anchor placement relative to fissures or other defects in the annulus. The guide tool 520 is preferably about 15 to 25 centimeters long. The longitudinal axes of the shaft 530 and handle 540 of the guide tool 520 are preferably laterally offset from the longitudinal axis of the distal tip 525 of the guide tool 520 (see FIG. 5A). Such a configuration prevents the guide tool 520 from obstructing the surgeon's view of the disc D, and particularly of the fissure F in the disc D. The longitudinal axis of the shaft 530 of the guide tool 520 is preferably offset about 2 to 5 millimeters lateral to the longitudinal axis of the distal end 525 of the guide tool 520 (note that FIG. 5A is not drawn to scale). The guide tool 520 is preferably made of metal or plastic.

Figure 6A:
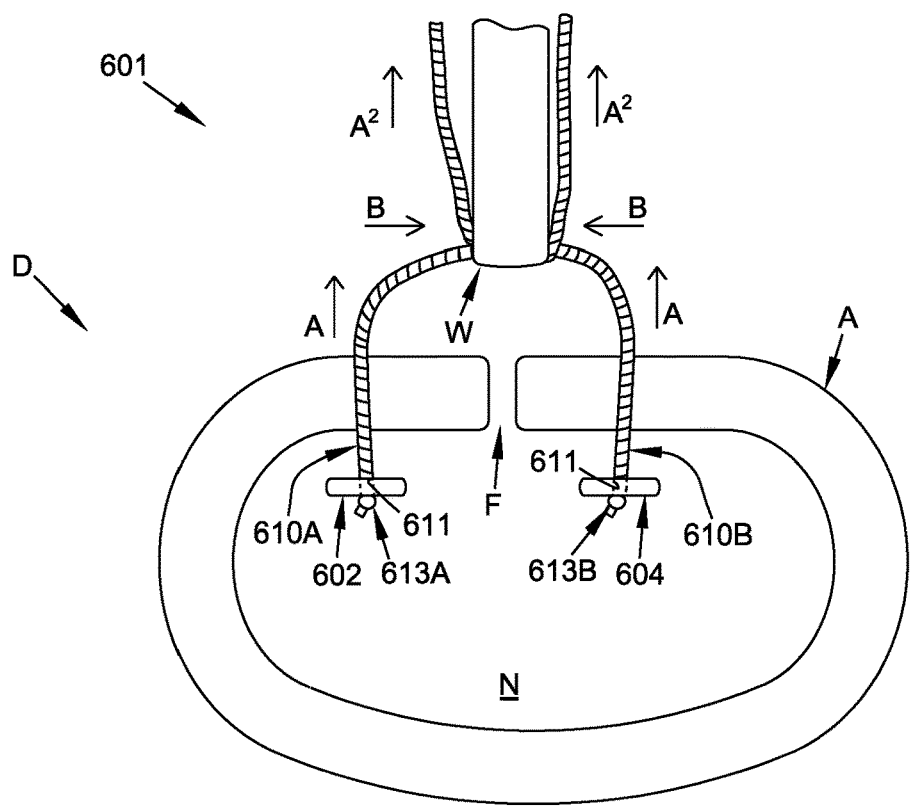
FIG. 6A is a schematic view showing another preferred form of apparatus for closing a fissure in the annulus.

FIG. 6A is a schematic view showing another form of the present invention. More particularly, FIG. 6A shows apparatus 601 for closing a fissure or tear F in the annulus A of an intervertebral disc D so as to prevent the extrusion of nucleus N from the disc. In FIG. 6A, first and second transverse anchor components 602, 604 are shown disposed on either side of the fissure F in the posterior annulus. The transverse anchor components 602, 604 are preferably initially positioned inside the nucleus N about 3 to 5 millimeters anterior to the inner surface of the posterior annulus in order to provide room for the transverse anchor components 602, 604 to turn from their insertion orientation (i.e., perpendicular to the posterior annulus) to their deployed orientation (i.e., parallel to the posterior annulus). Knots 613A, 613B are shown in the respective distal ends of two flexible longitudinal fixation components 610A and 610B, which are passed through holes 611 in the transverse anchor components 602, 604. The transverse anchor components 602, 604 are preferably inserted through the annulus using a needle-like insertion device such as the needle-like insertion apparatus 122 disclosed above. The central portions of the flexible longitudinal fixation component 610A, 610B are seen within the jaws of a welding tool W. The distal ends of the flexible longitudinal fixation components 610A, 610B are seen extending along the sides of the shaft of the welding tool W. The flexible longitudinal fixation components 610A, 610B enter one side of the jaws of the welding tool W and exit on the other side of the jaws of the welding tool.

Thus, with this form of the invention, two separate flexible longitudinal fixation components (e.g., filaments) 610A, 610B are provided, each with its own transverse anchor component (e.g., bar anchor) 602, 604, with the two flexible longitudinal fixation components 610A, 610B being united with one another only after their associated transverse anchor components 602, 604 have been set in the disc.

Figure 6B:
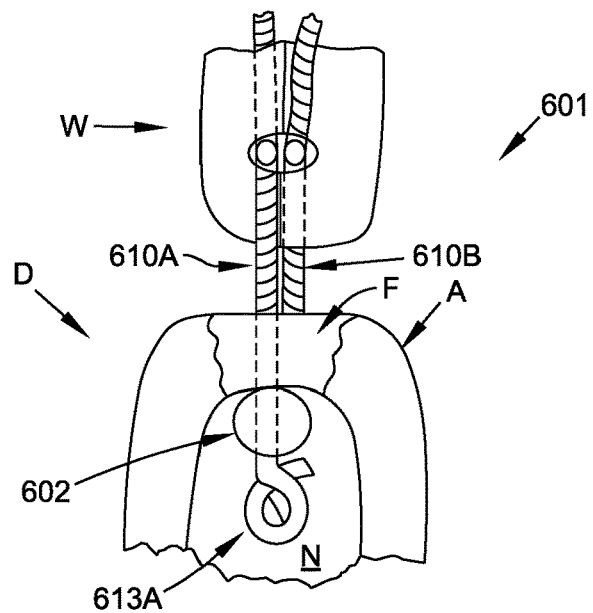
FIG. 6B is a schematic view showing the apparatus of FIG. 6A closing the fissure in the annulus.
Figure 6C:
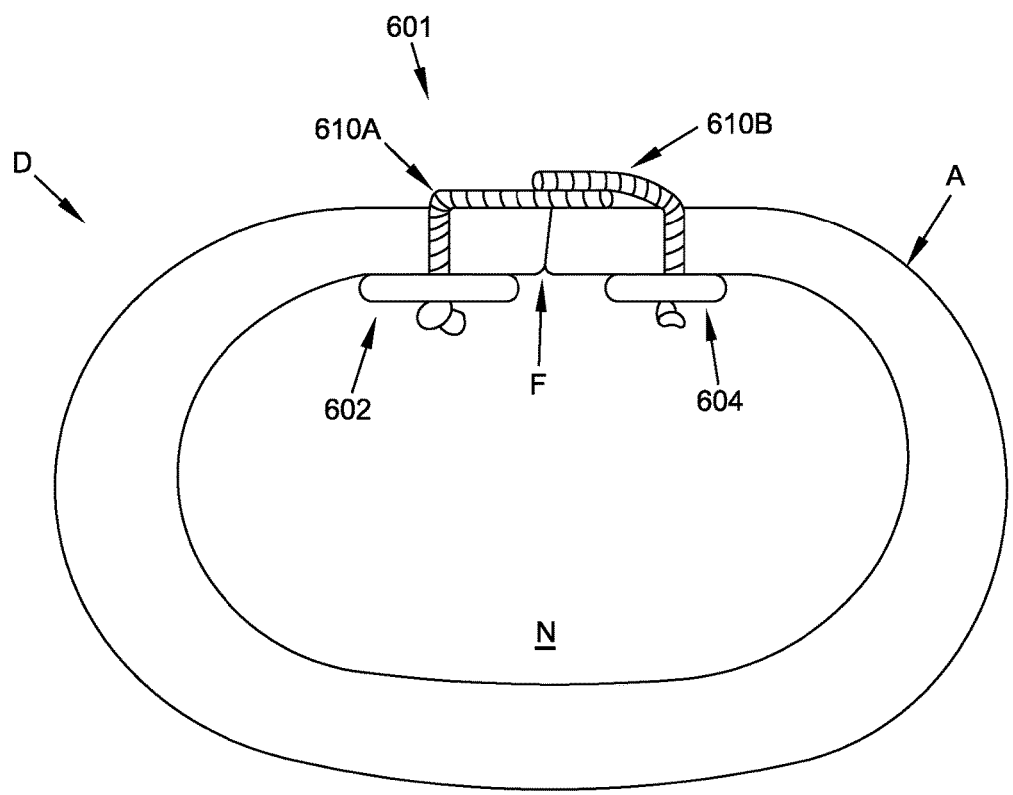
FIG. 6C is another schematic view showing the apparatus of FIG. 6A closing the fissure in the annulus.

In accordance with the present invention, axial tensile forces of about 6 N to 60 N or more are applied to the flexible longitudinal fixation components 610A, 610B generally perpendicular to the posterior surface of the annulus in the direction A (FIG. 6A) before the flexible longitudinal fixation components 610A, 610B are drawn together under lateral tension of about 10 N to 60 N or more applied generally parallel to the posterior surface of the annulus in the direction B and then they are locked together (e.g., by welding) under this lateral tension (FIGS. 6B and 6C). Such axial pretension forces are most preferably about 15 N to 50 N or more. Alternatively, such axial pretension forces are preferably 80% to 60% of the breaking strength of the flexible longitudinal fixation component 610A, 610B, when such breaking strength is measured of a single limb of such component or a loop of such component with or without knots or other stress risers in such component. Alternatively, such axial pretension forces could preferably be 50, 51, 52, 53, 54, 55, 56, 57, 58, 59, 81, 82, 83, 84, 85, 86, 87, 88, 89, less than 50, or more than 89%, of such breaking strength of the longitudinal fixation component.

Ten devices similar to that shown in FIG. 6A were applied to the posterior of human cadaver intervertebral discs. Anchors (i.e., the transverse anchor components 602, 604) of all devices were inserted about 10 to 12 mm into the discs. Axial tensile forces, applied in the direction A, of approximately 25 N were applied to the flexible longitudinal fixation components 610A, 610B of five of the devices ("axial pre-tensioned" group) before welding the flexible longitudinal fixation components 610A, 610B under lateral tension. Tension in the direction A was not applied to the flexible longitudinal fixation components 610A, 610B of five additional devices ("non-axial pre-tensioned" group). The welding tool W was used to apply approximately 15 N lateral tensile forces on the flexible longitudinal fixation components 610A, 610B of devices in both the "axial pre-tensioned" and "non-axial pre-tensioned" groups. Such lateral tensile forces applied by the welding tool W were parallel to the posterior surface of the disc in the directions B, which is generally parallel to the plane of the longitudinal axis of the deployed transverse anchor components 602, 604, which rest against the inner surface of the posterior annulus. Those lateral tension forces are also generally perpendicular to the portion of the flexible longitudinal fixation component 610A, 610B that lies within and immediately adjacent to the transverse anchor component 602, 604.

High strength sutures were placed under the welded flexible longitudinal fixation components 610A, 610B and the sutures were pulled up to 15 N with a MTS machine while that machine recorded axial displacement. Average displacements of 10.340 mm and 5.526 mm were recorded for the non-axial pre-tensioned and the axial pre-tensioned groups, respectively. In other words, the transverse anchor components 602, 604 of the non-axial pre-tensioned group moved about twice as much as the transverse anchor components 602, 604 of the axial pre-tensioned groups. That difference was highly significant (P=0.006). Axial cross-sections of discs D after testing showed that the transverse anchor components 602, 604 of all devices were pulled through disc tissue towards the posterior of the annulus of all specimens. The findings show axial pretension forces of about 25 N before applying lateral tension forces of about 15 N in a plane generally perpendicular to the axial pre-tension forces, for example with welding tools or other locking mechanisms or devices, pulls the transverse anchor components 602, 604 towards the inner surface of the posterior annulus before the flexible longitudinal fixation components 610A, 610B are locked together. This helps maintain tension on the locked flexible longitudinal fixation components 610A, 610B and prevents or minimizes slack from occurring in the locked flexible longitudinal fixation components 610A, 610B. Such slack, which measured almost 5 mm in the test conducted, allows the edges of the previously-closed sides of the fissure F in annulus A to separate. Nucleus material N (or prosthetic devices deployed in the nucleus) more easily escapes through such opened fissures.

It was also discovered that the axial pre-tension forces applied generally perpendicular to the posterior surface of the disc D should be followed by a preferably 10 N to 40 N lateral tension (or higher) applied parallel to the posterior surface of the annulus (i.e., the axial pre-tension forces should be followed by a lateral closing tension). The first, "pre-tension" force pulls the transverse anchor components 602, 604 towards the inner surface of the annulus. The second, "lateral closing" tension force holds the transverse anchor components 602, 604 in that location and pulls or holds the edges of the annulus, on the two sides of the fissure, together. The second lateral closing tension force is most preferably about 15 N to 25 N.

In a separate test, it was determined that the force required to push a 4 mm spherical probe through fissures closed with the apparatus 601 (welded after applying about a 25 N axial pre-tension force followed by a 15 N lateral closing force applied perpendicular to the first axial tensile force) was 1.6 times higher than such force in fissures closed with devices locked with only a 6 N lateral tensile force and without applying an axial pre-tension force. The force required to push such probes through fissures closed with the apparatus 601 (locked after applying both the axial pre-tension force and the lateral closing force) were 4.04 times that of control (P=0.014), while such force was 2.47 times that of control for devices locked with only the 6 N lateral tensile force and without an axial pre-tension force (P=0.401).

It was also discovered that the transverse anchor components 602, 604 should preferably be inserted 6 to 10 millimeters into discs D so as to minimize the distance that the transverse anchor components 602, 204 had to be pulled through the nucleus N so as to arrive against the inner surface of the annulus. Depth stops on the sides of the needle-like insertion device used to insert the transverse anchor components 602, 604 into discs D should preferably be located 7 to 11 millimeters proximal to the distal ends or tips of the needle-like insertion device so as to ensure the desired insertion depth.

FIG. 6C is a schematic view showing the apparatus 601 of FIG. 6A holding a fissure F closed so as to prevent the extrusion of nucleus N. Axial tension on the distal ends of the flexible longitudinal fixation components 610A, 610B in the A and $A_2$ direction (FIG. 6A) pulled the transverse anchor components 602, 604 through the nucleus N about 3 to 5 millimeters and against the inner surface of the posterior annulus. Subsequent lateral tension on the flexible longitudinal fixation components 610A, 610B in directions B (FIG. 6A) pulled the fissure F closed. The flexible longitudinal fixation components 610A, 610B were welded under tension after applying tension repeatedly in directions A, $A_2$, & B.

It should be appreciated that with the construction shown in FIGS. 6A-6C, each of the flexible longitudinal fixation components 610A, 610B is set separately from one another, and the separate flexible longitudinal fixation components 610A, 610B are only united with one another after their associated transverse anchor components 602, 604 are set in the disc. As a result, as each of the flexible longitudinal fixation components 610A, 610B has its associated transverse anchor component 602, 604 set in the disc, the seating of each transverse anchor component 602, 604 can be separately tested (e.g., with an appropriate tug on the free end of the associated flexible longitudinal fixation component 610A, 610B) so as to confirm proper placement and seating. Significantly, since each filament/anchor pair (i.e., each flexible longitudinal fixation component/transverse anchor component pair) is set separately, any difficulty associated with one filament/anchor deployment is isolated from another filament/anchor deployment. Thus, if one filament/anchor deployment needs to be revised, it does not require revision of any other filament/anchor deployment. This is a significant advantage in clinical practice.

Figure 7:
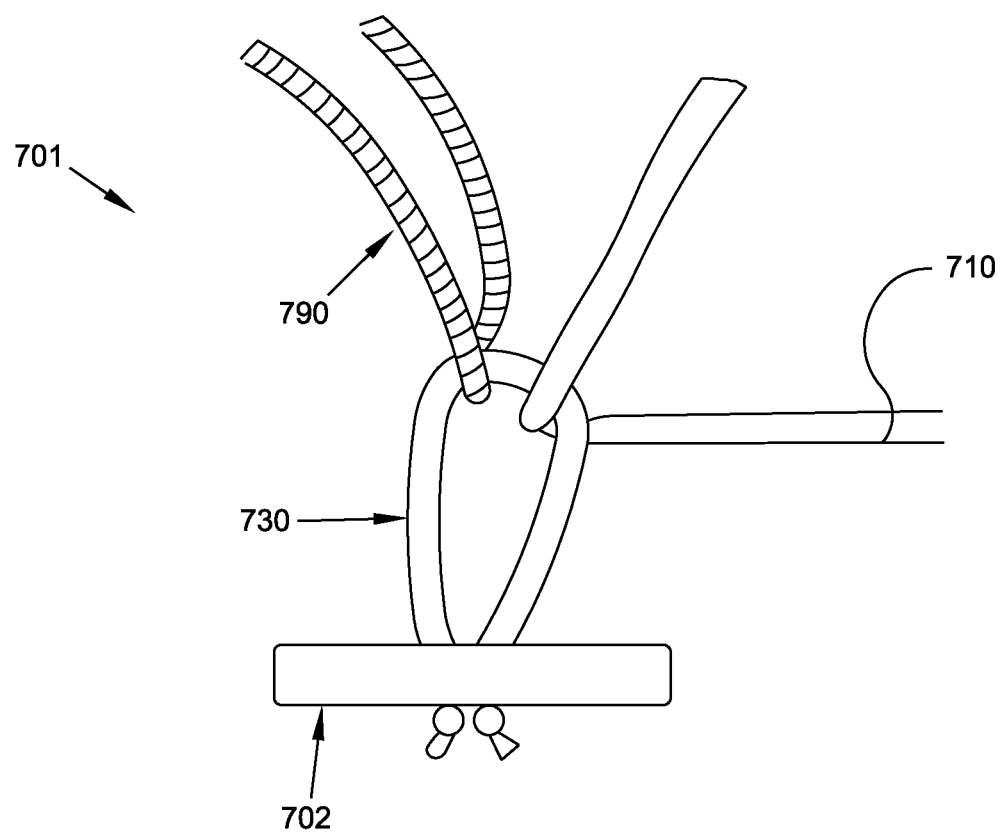
FIG. 7 is a schematic view showing still another preferred form of apparatus for closing a fissure in the annulus.

FIG. 7 is a schematic view of another form of the present invention. More particularly, the apparatus 701 is generally similar to the apparatus 401 disclosed above, with a shorter flexible longitudinal fixation component 730 connecting longer flexible longitudinal fixation component 710 to transverse anchor component 702. However, a second flexible longitudinal component 790 is seen passing through the space formed by the transverse anchor component 702 and the smaller flexible longitudinal fixation component 730. The ends of the second flexible longitudinal component 790 pass through the hole in the annulus created by the needle-like insertion device which sets the transverse anchor component 702. Axial tension on the ends of the second flexible longitudinal component 790, generally perpendicular to the posterior surface of the annulus, pulls the transverse anchor component 702 against the inner surface of the posterior annulus before the longer flexible longitudinal fixation components 710 are welded or interlocked under tension. The second flexible longitudinal component 790, such as a 3-0 or 4-0 suture, preferably breaks at about 15 N to 40 N or more, which releases that component from the smaller flexible longitudinal fixation component 730 and the transverse anchor component 702 after the transverse anchor component 702 is pulled through the nucleus N to seat against the inner surface of the posterior annulus. Alternatively, tension on both ends of the second flexible longitudinal component 790 could preferably pull the transverse anchor component 702 against the inner surface of the posterior annulus, then tension on a single end of that second flexible longitudinal component 790 will pull the second flexible longitudinal component 790 from the loop of the smaller flexible longitudinal fixation component 730 and then from the disc.

The ends of the longer flexible longitudinal fixation component 710A, 710B are preferably loaded into the jaws of a welding device W (Tornier, Edina Minn.) as seen in FIG. 6A, which tensions the flexible longitudinal fixation component 710A, 710B in the lateral direction (i.e., parallel to the posterior surface of the annulus). The welding device W is preferably pulled away from the disc to tension the flexible longitudinal fixation component 710A, 710B in the first direction $A_2$ a second, third, fourth or more times after applying lateral tension in the second direction B. Alternative methods or devices may be used to repeatedly tension the flexible longitudinal fixation component 710A, 710B in the first or second directions.

Figure 8:
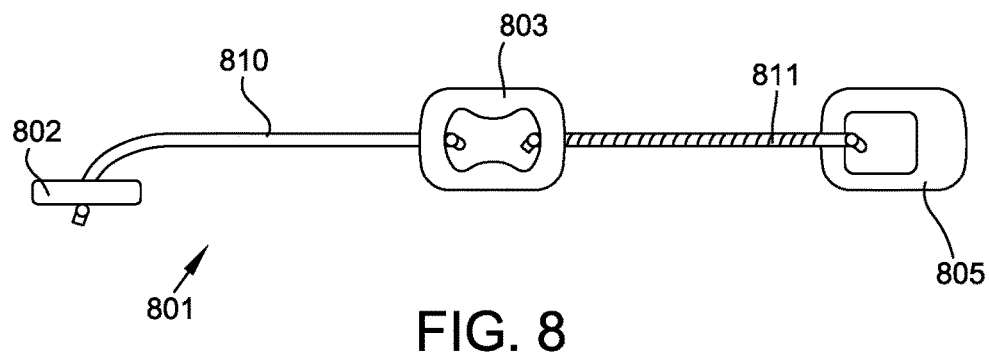
FIG. 8 is a schematic view showing yet another preferred form of apparatus for closing a fissure in the annulus.

FIG. 8 is a schematic view of another form of the present invention. In this form of the invention, apparatus 801 comprises a handle-like component 803 which is provided at the proximal end of a flexible longitudinal fixation component 810. A transverse anchor component 802 is seen on the distal end of that flexible longitudinal fixation component 810. The handle 803 facilitates manipulation of the flexible longitudinal fixation component 810, especially for the application of tensile forces (both axial and lateral) to that component. The flexible longitudinal fixation component 810 is cut to release the handle 803 after the flexible longitudinal fixation component 810 is welded or locked to a second such flexible longitudinal fixation component 810.

A second flexible longitudinal fixation component 811 may be attached to the proximal end of the handle component 803. A second handle component 805 is preferably attached to the proximal end of the second flexible longitudinal fixation component 811. The second handle component 805 is pulled to pull the anchor component 802 against the inner surface of the posterior annulus. The second flexible longitudinal fixation component 811 preferably breaks at about 15 N to 40 N of tension or more. Alternatively, the first handle 803 could break from the proximal end of the flexible longitudinal fixation component 810 at such preferred force, which eliminates the need for the second handle component 805.

The handle component 803 helps surgeons apply the preferred axial pretension force without exceeding such force, which could injure the annulus or break the flexible longitudinal fixation component 810.

Figure 9:
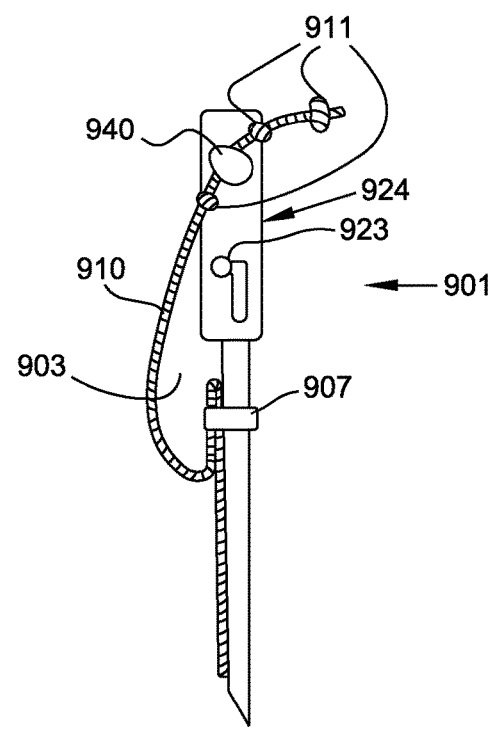
FIG. 9 is a schematic view showing another preferred form of needle-like insertion device for deploying apparatus for closing a fissure in the annulus.

Alternative methods or devices may be used to facilitate the application of tension in an axial direction on the flexible longitudinal fixation component 810. For example, as seen in FIG. 9, a bead 940 could be threaded over the proximal end of such fixation component. A certain predetermined force could pull the bead over a knot tied in the flexible longitudinal fixation component, proximal to the bead, so as to ensure surgeons apply sufficient tension on the flexible longitudinal fixation component.

More particularly, FIG. 9 is a schematic view of a needle-like insertion device 901 which constitutes an alternative embodiment of the needle-like anchor insertion device 122 shown in FIG. 1B. A loop 903 formed in the central portion of the flexible longitudinal fixation component 910 is seen under an elastic sleeve 907 that was inserted over the shaft of the needle-like insertion device 722. The loop 903 is pulled from under the elastic sleeve as the surgeon pulls the needle-like insertion device from the patient, which completely releases the flexible longitudinal fixation component 910 from the needle-like insertion device 901. The transverse anchor component lies within the needle-like insertion device 901 near the distal tip of the needle-like insertion device. The distal portion of the flexible longitudinal fixation component 910 is fastened to the transverse anchor.

A bead 940 is seen near the proximal end of the flexible longitudinal fixation component 910. Knots 911 in the flexible longitudinal fixation component 910, proximal and distal to the bead 940, keep the bead 940 near the proximal end of the flexible longitudinal fixation component 910. Tension on the bead 940, after placing the transverse anchor component into the disc, pulls the transverse anchor component in the first direction and against an inner layer of the posterior annulus. The bead 940 may preferably slide over the knot 911 just proximal to the bead 940 when sufficient force is applied to the bead.

A projection 923 is seen on the side of the handle 924 of the needle-like insertion device 901. The projection 923 is attached to the stylet (not shown) within the needle-like insertion device. Axial rotation of the stylet enables advancement of the stylet in a distal direction, much like a bolt-action gun, which forces the transverse anchor component from the needle-like insertion device. Alternatively, a projection from the stylet could extend through the proximal end of the handle 924 of the needle-like insertion device. Like a ballpoint pen, pressure on the projection 923 could advance a spring-loaded stylet, which forces the transverse anchor component from the needle-like insertion device 901.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for closing a fissure in a region of tissue having an inner surface and an outer surface, the method comprising:
    providing a first transverse anchor having a first surface, a second surface and a hole extending from the first surface to the second surface, and a first flexible longitudinal fixation component having a first end and a second end, wherein the first flexible longitudinal fixation component is passed through the hole in the first transverse anchor and secured to the first transverse anchor with a first knot tied on the second surface of the first transverse anchor;
    providing a second transverse anchor having a first surface, a second surface and a hole extending from the first surface to the second surface, and a second flexible longitudinal fixation component having a first end and a second end, wherein the second flexible longitudinal fixation component is passed through the hole in the second transverse anchor and secured to the second transverse anchor with a second knot tied on the second surface of the second transverse anchor;
    positioning the first surface of the first transverse anchor on one side of the fissure and against the inner surface of the tissue, with the second end of the first flexible longitudinal fixation component extending to the outer surface of the tissue on the first side of the fissure;
    positioning the first surface of the second transverse anchor on the second side of the fissure and against the inner surface of the tissue, with the second end of the second flexible longitudinal fixation component extending to the outer surface of the tissue on the second side of the fissure;
    tensioning the first flexible longitudinal fixation component and second flexible longitudinal fixation component so as to reduce the size of the fissure; and
    securing the first flexible longitudinal fixation component to the second flexible longitudinal fixation component.

2. A method for closing a fissure in the annulus of an intervertebral disc, comprising:
    providing a first transverse anchor having a first surface, a second surface and a hole extending from the first surface to the second surface, and having a first filament extending therefrom, wherein the first filament comprises a first end and a second end, and further wherein the first filament is passed through the hole in the first transverse anchor and secured to the first transverse anchor with a first knot tied on the second surface of the first transverse anchor;
    providing a second transverse anchor having a first surface, a second surface and a hole extending from the first surface to the second surface, and having a second filament extending therefrom, wherein the second filament comprises a first end and a second end, and further wherein the second filament is passed through the hole in the first transverse anchor and secured to the first transverse anchor with a second knot tied on the second surface of the second transverse anchor;
    advancing said first transverse anchor through the annulus of the intervertebral disc on one side of the fissure so that the first transverse anchor is disposed against an inner surface of the annulus and the first filament extends through the wall of the annulus on one side of the fissure, and advancing said second transverse anchor through the annulus of the intervertebral disc on a second side of the fissure so that the second transverse anchor is disposed against an inner surface of the annulus and the second filament extends through the wall of the annulus on the second side of the fissure;

applying tension to the first and second filaments so as to close the fissure; and welding the first filament to the second filament.

* * * * *